(12) United States Patent
Nguyen et al.

(10) Patent No.: US 12,157,102 B2
(45) Date of Patent: Dec. 3, 2024

(54) ROTATABLE DEVICE CONTAINING WAFERS FOR DNA PROCESSING

(71) Applicant: MICROSOFT TECHNOLOGY LICENSING, LLC, Redmond, WA (US)

(72) Inventors: Bichlien H. Nguyen, Seattle, WA (US); Douglas P. Kelley, Sammamish, WA (US); Karin Strauss, Seattle, WA (US); Robert Carlson, Seattle, WA (US); Hsing-Yeh Parker, Woodinville, WA (US); John Mulligan, Redmond, WA (US); Luis H. Ceze, Redmond, WA (US); Yuan-Jyue Chen, Seattle, WA (US); Douglas Carmean, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 17/863,033

(22) Filed: Jul. 12, 2022

(65) Prior Publication Data
US 2022/0347645 A1 Nov. 3, 2022

Related U.S. Application Data

(63) Continuation of application No. 15/986,425, filed on May 22, 2018, now Pat. No. 11,439,970.

(51) Int. Cl.
*B01J 19/00* (2006.01)

(52) U.S. Cl.
CPC .. *B01J 19/0046* (2013.01); *B01J 2219/00277* (2013.01); *B01J 2219/0068* (2013.01); *B01J 2219/00722* (2013.01)

(58) Field of Classification Search
CPC ............. B01J 2219/00488; B01J 2219/00536
See application file for complete search history.

(56) References Cited

U.S. PATENT DOCUMENTS

| | | | | |
|---|---|---|---|---|
| 5,534,328 A | * | 7/1996 | Ashmead | ........... B01F 33/30 210/150 |
| 6,582,662 B1 | * | 6/2003 | Kellogg | ........... B01F 25/23 422/50 |
| 2016/0229884 A1 | | 8/2016 | Indermuhle | |

* cited by examiner

*Primary Examiner* — Natalia Levkovich
(74) *Attorney, Agent, or Firm* — Benjamin Keim; Newport IP, LLC

(57) ABSTRACT

A system includes a synthesizer unit having a fluid input to receive fluids and a communication input to receive commands to synthesize data-encoded DNA sequences and cleave the DNA. A first flexible chemistry reaction chamber module may be fluidically coupled to the synthesizer unit to receive the data-encoded DNA sequences and amplify the sequences. A deposition unit may be fluidically coupled to the first flexible chemistry reaction chamber module to receive the amplified DNA sequences and encapsulate the amplified DNA sequences into one or more wells in a storage plate for storage and retrieval to and from a plate storage unit. Retrieved DNA may be processed and read by further units.

18 Claims, 15 Drawing Sheets

ROTATABLE DEVICE CONTAINING WAFERS FOR DNA PROCESSING

CROSS-REFERENCE TO RELATED APPLICATION

This application is a continuation of U.S. patent application Ser. No. 15/986,425, filed May 22, 2018, the content of which application is hereby expressly incorporated herein by reference in its entirety.

BACKGROUND

Current storage technologies can no longer keep pace with exponentially growing amounts of data. Synthetic DNA offers an attractive alternative due to its potential information density of ~$10^{18} B/mm^3$, $10^7$ times denser than magnetic tape, and potential durability of thousands of years. Recent advances in DNA data storage have highlighted technical challenges, in particular, with coding and random access, but have stored only modest amounts of data in synthetic DNA.

SUMMARY

A system includes a synthesizer unit having a fluid input to receive fluids and a communication input to receive commands to synthesize data-encoded DNA sequences and cleave the DNA. A first flexible chemistry reaction chamber module may be fluidically coupled to the synthesizer unit to receive the data-encoded DNA sequences and amplify the sequences. A deposition unit may be fluidically coupled to the first flexible chemistry reaction chamber module to receive the amplified DNA sequences and encapsulate the amplified DNA sequences into one or more wells in a storage plate for storage and retrieval to and from a plate storage unit.

A method includes synthesizing data-encoded DNA sequences and cleaving the DNA sequences via a synthesizer unit having a fluid input to receive fluids and a communication input to receive commands to synthesize data-encoded sequences and cleave the DNA, amplifying the DNA sequences via a first flexible chemistry reaction chamber module fluidically coupled to the synthesizer unit, and receiving the amplified DNA sequences and encapsulating the amplified DNA sequences via a deposition unit fluidically coupled to the first flexible chemistry reaction chamber module into one or more wells in a storage plate for storage and retrieval to and from a plate storage unit.

A machine-readable storage device has instructions for execution by a processor of the machine to perform operations. The operations include controlling synthesizing data-encoded DNA sequences and cleaving the DNA sequences via a synthesizer unit having a fluid input to receive fluids and a communication input to receive commands to synthesize data-encoded sequences and cleave the DNA, controlling amplifying the DNA sequences via a first flexible chemistry reaction chamber module fluidically coupled to the synthesizer unit, and controlling receiving of the amplified DNA sequences and encapsulating the amplified DNA sequences via a deposition unit fluidically coupled to the first flexible chemistry reaction chamber module into one or more wells in a storage plate for storage and retrieval to and from a plate storage unit.

DETAILED DESCRIPTION

Figure 1A:
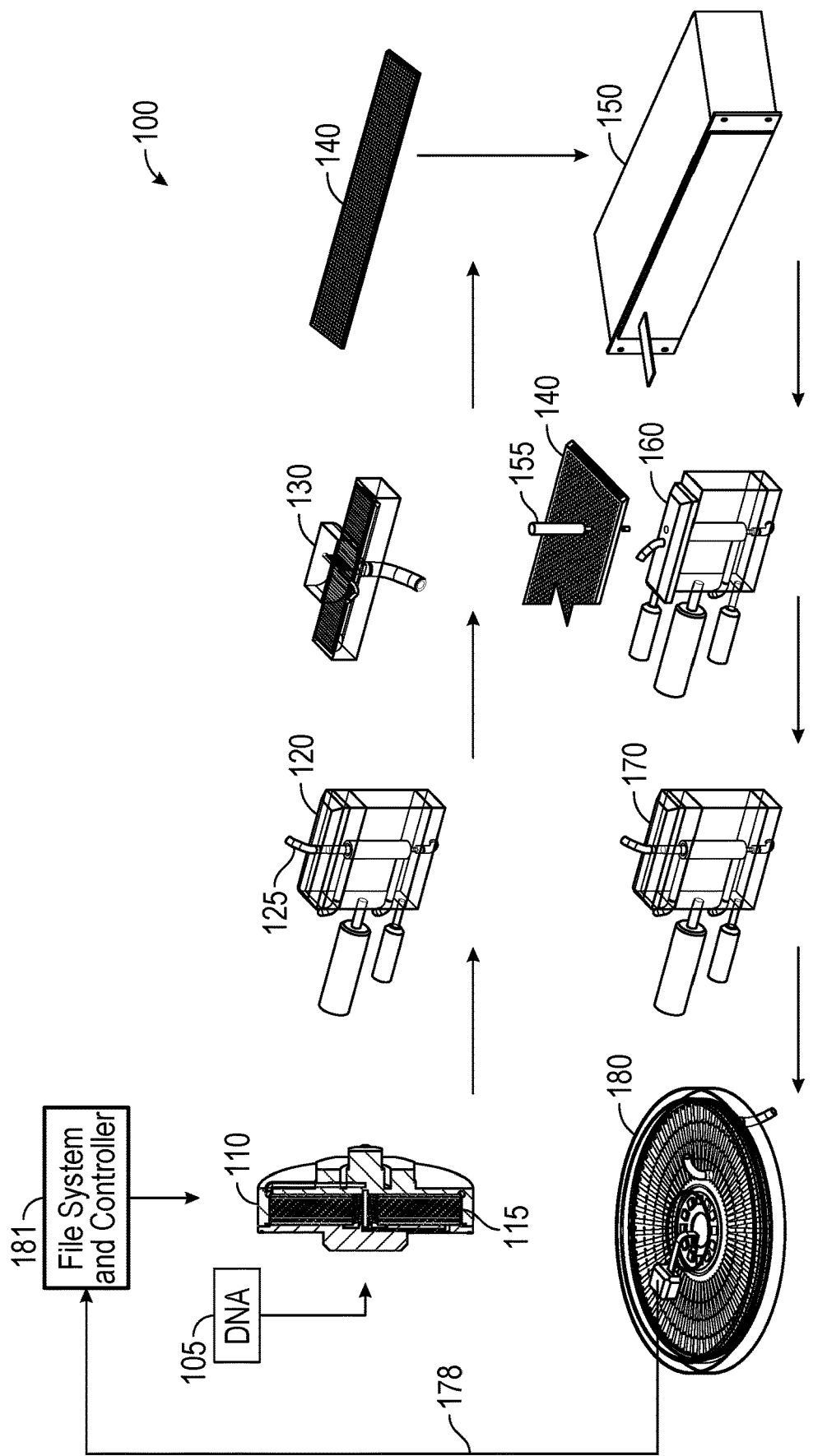
FIG. 1A is a block pictorial flow diagram of a data-encoded DNA manufacturing, storage, and access system according to an example embodiment.

In the following description, reference is made to the accompanying drawings that form a part hereof, and in which is shown by way of illustration specific embodiments which may be practiced. These embodiments are described in sufficient detail to enable those skilled in the art to practice the inventive subject matter, and it is to be understood that other embodiments may be utilized and that structural, logical, and electrical changes may be made without departing from the scope of the present inventive subject matter. The following description of example embodiments is, therefore, not to be taken in a limited sense, and the scope of the present inventive subject matter is defined by the appended claims.

The functions or algorithms described herein may be implemented in software in one embodiment. The software may consist of computer-executable instructions stored on computer-readable media or computer-readable storage device such as one or more non-transitory memories or other type of hardware-based storage devices, either local or networked. Further, such functions correspond to modules, which may be software, hardware, firmware, or any combination thereof. Multiple functions may be performed in one or more modules as desired, and the embodiments described are merely examples. The software may be executed on a digital signal processor, ASIC, microprocessor, or other type of processor operating on a computer system, such as a personal computer, server or other computer system, turning such computer system into a specifically programmed machine. The term "module" is also used herein to refer to various mechanical devices, systems, and units for synthesizing, processing, and sequencing DNA.

The functionality can be configured to perform an operation using, for instance, software, hardware, firmware, or the like. For example, the phrase "configured to" can refer to a logic circuit structure of a hardware element that is to implement the associated functionality. The phrase "configured to" may also refer to structural modifications of physical components to accomplish a stated function. The phrase "configured to" can also refer to a logic circuit structure of a hardware element that is designed to implement the coding design of associated functionality of firmware or software.

Furthermore, methods for controlling various devices and mechanical components, such as robots, microfluidic tubes and valves, actuators, and the like may be implemented as a method, apparatus, or article of manufacture using standard programming and engineering techniques to produce software, firmware, hardware, or any combination thereof to control a computing device to implement the methods. The term "article of manufacture," as used herein, is intended to encompass a computer program accessible from any computer-readable storage device or media. Computer-readable storage media can include, but are not limited to, magnetic storage devices, e.g., hard disk, floppy disk, magnetic strips, optical disk, compact disk (CD), digital versatile disk (DVD), smart cards, flash memory devices, among others. In contrast, computer-readable media, i.e., not storage media, may additionally include communication media such as transmission media for wireless signals and the like.

Recent advances in DNA data storage have highlighted technical challenges, in particular, coding, and random access, but have stored only modest amounts of data in synthetic DNA.

High throughput synthesis and sequencing of DNA results in immersing DNA into fluids, exposing the DNA to light, moving batches of DNA around, etc. The term "fluids," as used herein, refers to liquids used in various DNA processes, including at least DNA synthesis, amplification, preparation for sequencing, and sequencing. Creating an entirely new system to perform these tasks, yet protect associated electronics, may be expensive. Various embodiments of the present inventive subject matter reuse equipment, pipelines, and automation developed for semiconductor fabrication for these purposes, and may also utilize newly designed equipment.

DNA synthesis consists of exposing a surface to sequential chemical baths. In various embodiments, the surface may be formed of glass or silicon, silica coatings, silicon dioxide, aluminum oxide, silica coatings, titanium oxide, other metal oxides, metal nitrides, graphene and graphites, or various organic polymer coatings. The surface can be solid, porous, or with various patterned topographies. The surface may be patterned following commonly used semiconductor processing and may also be functionalized for DNA synthesis. Synthesis may also include activating electronics on the surface, shining light selectively on parts of the surface, or depositing selectively on parts of the surface. In various embodiments, such synthesis steps may be done using silicon fabrication equipment in a fab-like pipeline.

Sequencing also utilizes operations similar to synthesis and may include the use of cameras to capture optical features on the DNA attached to the surface, or the use of nanopores or other electrical sequencing technology that benefits from the bulk fluidics provided by the semiconductor fabrication equipment.

In some embodiments, wafer-shaped substrates are used for both synthesis and sequencing of DNA in a DNA synthesis/sequencing unit. Chips, wafers, synthesis surfaces, and sequencing surfaces may be brought to fluids and other equipment that operates over the DNA. Automation equipment may use devices such as wafer boats to move chips/wafers and fluidics (microfluidics, microfluidics, tubes, etc.) to transfer DNA between equipment. Much of the same equipment used in semiconductor fabrication, such as lithography, equipment to expose to chemicals in batch, testing equipment to drive electronics in chips/wafers, and other equipment, along with newly designed devices for processing DNA, may be used in various embodiments.

Large-scale DNA manufacturing is challenging due to the level of automation and delivery/removal of chemical reagents to surfaces where the DNA is grown. In one embodiment, a rotatable stacked assembly of wafers for DNA synthesis is mounted on an axis in a chamber of a DNA synthesis module or unit. Stacking of the wafers provides an increased surface area per volume for processing DNA. Rotation of the stack about the axis aids in centrifuging reagents out of the space between the wafers. Pressurization of the chamber or connecting the chamber to a vacuum source further assists with complete removal of used reagents and addition of new reagents in the chamber.

The wafers where the DNA grows may be mounted on a stack. The stack is mounted on an axis. If wafers need to communicate with the exterior (optical control, pH-based electronic control, and mechanical throttling control solutions), the wafers are connected via flat flex circuits, wirelessly via transceivers, or another connector. The wafers may be planar or have spacers to separate the wafers, give the stack more rigidity, and/or reduce the empty/reagent space in the chamber.

For DNA synthesis, the wafers may be exposed to reagents in series, interspersed with activation of elements on the wafers (light sources for optical control, electrodes for pH-based measurements or thermal control, and throttles for mechanical control). The reagent delivery and removal are challenging for a stack of wafers.

By enclosing the stack of wafers in a chamber and connecting the chamber to a pressure control source, fast delivery and removal of reagent are provided. First, the chamber is emptied by spinning the wafers and applying a positive pressure via an inert gas to overcome a pressure gradient caused by the spinning. Once emptied, a valve is opened that lets the selected reagent in, completely filling the empty spaces in the chamber. Negative pressure in the chamber may be used to facilitate filling. Next, if needed, active elements in the chip are activated. Finally, spinning and positive pressure may be used again to remove the reagent from the chamber, leaving it ready for the next step/reagent.

Cleavage and deprotection of the DNA may also be performed stepwise or simultaneously in the chamber, either via pressurized gas injection, or a solution that is then heated, or a combination of pressurized gas injection and heating. Cleavage may be performed via one or more methods including acid, base, oxidative, reductive, thermal, photolytic, electrochemical, or enzymatic cleavage methods. The selection of reagents entering and exiting the chamber may be done via a configurable valve system.

The use of DNA for data storage and other applications involves DNA capture by solid-phase extraction or membrane filtration methods, filtration, size selection, mixing with other reagents, temperature cycling, and agitation. Various embodiments described herein may be used to fully automate such use. A DNA capture and elution system may be coupled with a flexible chemistry reaction chamber module having a chamber that can be opened/closed, heated/cooled, and agitated automatically.

Some automated solutions use magnetic bead extraction for DNA separation and pipettes for moving DNA solutions around test tubes. In one embodiment, a flexible chemistry reaction chamber module consists of a DNA capture and DNA release at a respective inlet and outlet of a chamber. A top plate and a bottom plate slide to open and close the chamber at appropriate times. The fluids may move in and out by gravity or due to pressurization of the incoming and outgoing tubing connected to the flexible chemistry reaction chamber module. In one embodiment, the DNA may be bound to magnetic or other kind of beads.

One use for the flexible chemistry reaction chamber module includes DNA size selection and polymerase chain reaction (PCR) amplification that may be performed after the DNA is synthesized by the DNA synthesis unit. Initially, the top and bottom of the unit are in the open position. A fluid carrying DNA coming from the DNA synthesis unit passes through the openings and is potentially recirculated. In the process, DNA is captured in the chamber by solid-phase extraction or membrane filtration methods and the remaining material flows away into a waste or reagent recycling unit. The capturing mechanism may be part of the filter or disposed to be exposed to DNA in or from the chamber. Next, the bottom is closed, and the DNA is eluted with a different fluid. Other reagents are added to prepare the contents for PCR. The top is closed and PCR is performed by temperature-cycling implemented by the heating/cooling system. Once complete, the bottom is opened, and the fluid passes through the second capture system (again, potentially recirculated to maximize capture). Finally, the DNA is eluted with a different fluid. In some embodiments, an additional opening may be provided for receiving stored capsules of DNA for rehydrating and otherwise processing the DNA.

Storage of DNA for long periods of time requires a system to preserve, organize, and densely pack large quantities of DNA in a small volume. Various embodiments meet these requirements and allow for automation of operations, namely, encapsulation, storage, retrieval, and recovery of the DNA.

In one embodiment, a set of slides or plates containing an array of spots, cavities, or wells (all referred to herein as wells) for preserving the DNA may be used. These plates are collectively stored in a storage container as "drawers" that slide in for storage and out for retrieval. Each plate may have features to facilitate capturing and movement by a robot and may also be identified with a unique visual feature like a 1D or 2D barcode or other (e.g., text or numbers). Metadata about what is stored and the location of the data-encoded DNA in the storage container may be recorded by a file system or database.

After it is synthesized, extracted, and/or amplified, the DNA is ready to be stored. The DNA may be stored in a single spot, cavity, or well, or aliquoted into multiple wells, either on the same plate, or different plates. DNA may also be added to existing, partially filled wells.

The cavities or wells are configured to capture the DNA and let the solvent flow out. This is accomplished either by a membrane at the bottom (or middle, or anywhere else in the cavity) that captures the DNA or by a different porous solid that fills the cavity and captures the DNA in its pores. DNA capture may also be facilitated by the use of electrostatic forces. Magnetic force may be used to capture DNA provided the DNA was bound to a magnetic bead in a prior step. Reagents may be added one or more times to make the DNA adhere to the beads. Once the DNA is captured in a well, more chemicals may be added to help preserve the DNA. If needed, the contents are dried and then the well may be hermetically sealed with a solid film, membrane, or other material, with inert gas included within the well with the dried contents. In further embodiments, wells may be individually sealed with local well-covering films, membranes, or other materials. Once the DNA is stored, the plate may be placed by a robot in the larger container for storage. A plate may not be entirely filled at once. Plates can be moved in and out of the large container in a reversible manner.

When it is time to recover the DNA, the location is determined by the file system or database from the metadata, and a robot retrieves the plate. The visual feature may also be used to identify a desired plate. The desired DNA is removed from the plate like a "blister package", where a rod-like plunger pushes the material out of the cavity and into another container that is used for de-encapsulation (e.g., chemical reaction chamber in the flexible chemistry reaction chamber module). In a further embodiment, a microfluidic board may be used to re-dissolve the DNA in a spot.

A rehydration unit, similar to a flexible chemistry reaction chamber module, may be used for de-encapsulation of retrieved stored DNA. After a blister of encapsulated DNA is dropped through a different or the same opening into the rehydration unit chamber, other reagents are added for de-encapsulation and rehydration. These reagents may be drained or recirculated using the same method as above (opening/closing inlet/outlet modules and using the capture system to hold the DNA in place). The de-encapsulated DNA may then be amplified via a flexible chemistry reaction chamber module similar to or the same as the above described flexible chemistry reaction chamber module.

Large-scale sequencing of DNA may be performed with the use of dense and highly parallel sequencers. Sequencing units may be aggregated onto large wafers that are placed into chambers for DNA delivery to the sequencing units. The same synthesis module may be used, but this time for sequencing, and is referred to as a sequencing module. The sequencing module may or may not use centrifugal forces and vacuum/pressure to add or evacuate reagents from the chamber. The sequencing module may be light-based (with light sources and sensors on chip), nanopore-based (like Oxford Nanopore Technologies (ONT)), or involve other operations (e.g., a light-based method such as PacBio or other sequencing technologies).

A DNA manufacturing, storage, and access system 100 is shown in a block pictorial flow diagram in FIG. 1A. System 100 may be used to mass produce, store, and access DNA encoded with data to provide an end-to-end solution. System 100 is first described at a high process flow level, with details of the components and processes described in further detail with respect to further figures.

A synthesis unit or module 110 receives a digital representation of DNA sequences 105, such as one or more polynucleotide sequences that encode data to be stored. In various embodiments, the sequences may be encoded with redundancy and various pairs of primers (ID sequences) to allow a level of random access of the data. One or more wafers may be rotatably mounted within a synthesis unit chamber 115, and fluids provided and evacuated from one or more ports. Synthesis of the DNA identified by the digital representation of DNA sequences 105 is performed by injecting fluids and draining them from the chamber 115 in succession. Rotation of the wafers may assist with fluid evacuation. The DNA is deprotected and cleaved by filling the chamber 115 with cleavage/deprotection reagents and heating up the chamber 115 for a few hours. Cleaving can occur in a range of pressures from 0-100 psi at varying temperatures and times.

A flexible chemistry reaction chamber module 120 receives fluids from the synthesis module 110, such as by fluidic piping 125, and processes the DNA. Processing the DNA may include amplifying the DNA for either storage or sequencing and checking to ensure the information was correctly encoded. The fluid may comprise a solvent containing the synthesized DNA. The flexible chemistry reaction chamber module 120 filters the fluids using filters designed to ensure the DNA sticks to the filters, while solvent flows to recycling or waste. The DNA may then be eluted into a flexible chemistry reaction chamber where additional reagents for the PCR or other processing may be added. The chamber may be alternately heated and cooled to thermocycle the DNA and reagents.

Once the flexible chemistry reaction chamber module 120 completes processing of the DNA, the DNA may be cleaned up by a similar filter. The cleaned DNA may be provided via fluidics to a storage plate deposition unit, or encapsulation unit 130, and the DNA is deposited in 20 different wells (or a different arbitrary number) of a high-density physical storage plate 140, along with other materials to preserve the DNA in capsules for long-term physical storage.

The physical storage plate 140 may be moved into a physical storage array/library 150 via a robot picker, or a person, for example. The storage array/library 150 may contain many such storage plates and may maintain an environment suitable for storage of DNA. The capsules may be dried for long-term storage via evaporation or baking at a temperature at which the DNA will not be damaged. Such drying may occur prior to placement of the plate 140 into the storage array/library 150, in some embodiments. Lowering the pressure below atmospheric pressure will also assist with evaporation. Low temperatures will reduce DNA degradation. In further embodiments, elevated temperatures may optionally be used to increase rate of evaporation. Lyophilization/freeze-drying may also be used.

To retrieve the DNA, storage plate 140 is retrieved from the storage array/library 150, and one (or more) of the capsules is "pressed out" of the physical storage plate by a plunger 155. The pressed-out capsule may be placed in a chamber of a retrieval/hydration unit 160 where new fluids are added, agitated, and optionally heated to dissolve the chemicals used for preservation and rehydrate the DNA. The use of warmed fluids may also help rehydrate, resuspend, and/or re-dissolve the DNA. Unit 160 may be similar in construction to flexible chemistry reaction chamber module 120 and may have an additional valve to seal a chamber for rehydration. In addition, unit 160 does not include filter material to allow the capsules to enter a rehydration chamber unimpeded.

Next, the retrieved DNA is filtered and may optionally go through PCR (using the same process as before) in a second flexible chemistry reaction chamber module 170, which may be identical to flexible chemistry reaction chamber module 120 in some embodiments. In some embodiments, the retrieved DNA may be able to be sequenced and read without the need for further PCR. Additional sequencing preparation steps can be performed in the flexible chemistry reaction chamber module 120 or a series of such modules, if necessary, such as by using magnets or electromagnets associated with the flexible chemistry reaction chamber module 120.

Finally, the DNA is moved into a sequencing unit 180, and a voltage may be applied to draw the DNA through nanopores, which read the data. Other methods of sequencing may be used in further embodiments. The sequencing unit 180 may have the same or similar construction as the synthesis module 110.

In various embodiments, the above components may be coupled via one or more tubes for transferring the DNA in various forms between the components, as well as one or more robots for transferring the storage plates 140 between components as well as controlling the plunger 155 to remove capsules from the plates 140 into chambers of one or more components. Robots may also be used to transfer the DNA using pipettes or test tubes. Various tubes and other components that come in contact with the DNA may be made of materials to which DNA does not easily adhere unless adherence is desired. Example materials that may be used to form the tubes include polypropylene, Kapton, and EPDM (ethylene propylene diene monomer) coated materials. Note that other elements may be designed such that DNA does adhere, such as various filters and other elements used to retain DNA while flushing fluids from components.

The synthesis module 110 then manufactures the specified digital representation of DNA sequences 105. When synthesis is complete, the synthesis module 110 deprotects, cleaves, and elutes the DNA from the wafer surface. A robot or fluidic tube transports the DNA in solution to the chamber in the flexible chemistry reaction chamber module 120 for size selection and PCR or other type of amplification or preparation for storage. In the process of producing DNA of a certain length, e.g., 150 nucleotides, shorter or longer strands may also be produced due to inefficiencies in the process. Size selection involves selecting DNA in the target size and rejecting strands that are much shorter or much longer. This process is referred to as size selection. In some implementations, filters may be tuned to capture DNA of a particular size range. Other methods include PCR, electrophoresis, and capture by solid-phase bound primers, which are complementary to the end sequences of synthesized oligonucleotides.

Once prepared, the DNA is moved, again via robot or tube, to the encapsulation unit 130, storage, retrieval and recovery system, and the DNA synthesized in one pool is stored, preserved, and sealed in one or more wells of one or more plates 140. The one or more plates 140 may then be stored in slots or drawers of one or more of storage array/library 150. A DNA pool can also be added to existing, partially filled well or cavities in one or more plates. In further embodiments, the DNA may be stored on a surface of the one or more plates 140. Wells, if used, may be cylindrical wells, or any other shape, having a desired cross section and/or depth.

When data is requested, the file system and controller 181 determines where the physical DNA can be found. The plate 140 is retrieved by a robotic system and the DNA is pushed out of its enclosure in a well and recovered. The recovered DNA may be added to another flexible chemistry reaction chamber module 160, which may operate as a retrieval/hydration unit where the DNA is separated from chemicals it may be preserved in. Next, it may be amplified, size selected, randomly accessed via a second flexible chemistry reaction chamber module 170, ligated, prepared for sequencing, etc. Finally, it is moved by a robot or tube to the sequencing unit 180, which then returns the electronic representation of the sequenced DNA to the file system and controller 181 as represented by line 178. The file system and controller 181 then invokes a decoder, which performs reassembly, error correction, and recovers the requested bits.

Figure 1B:
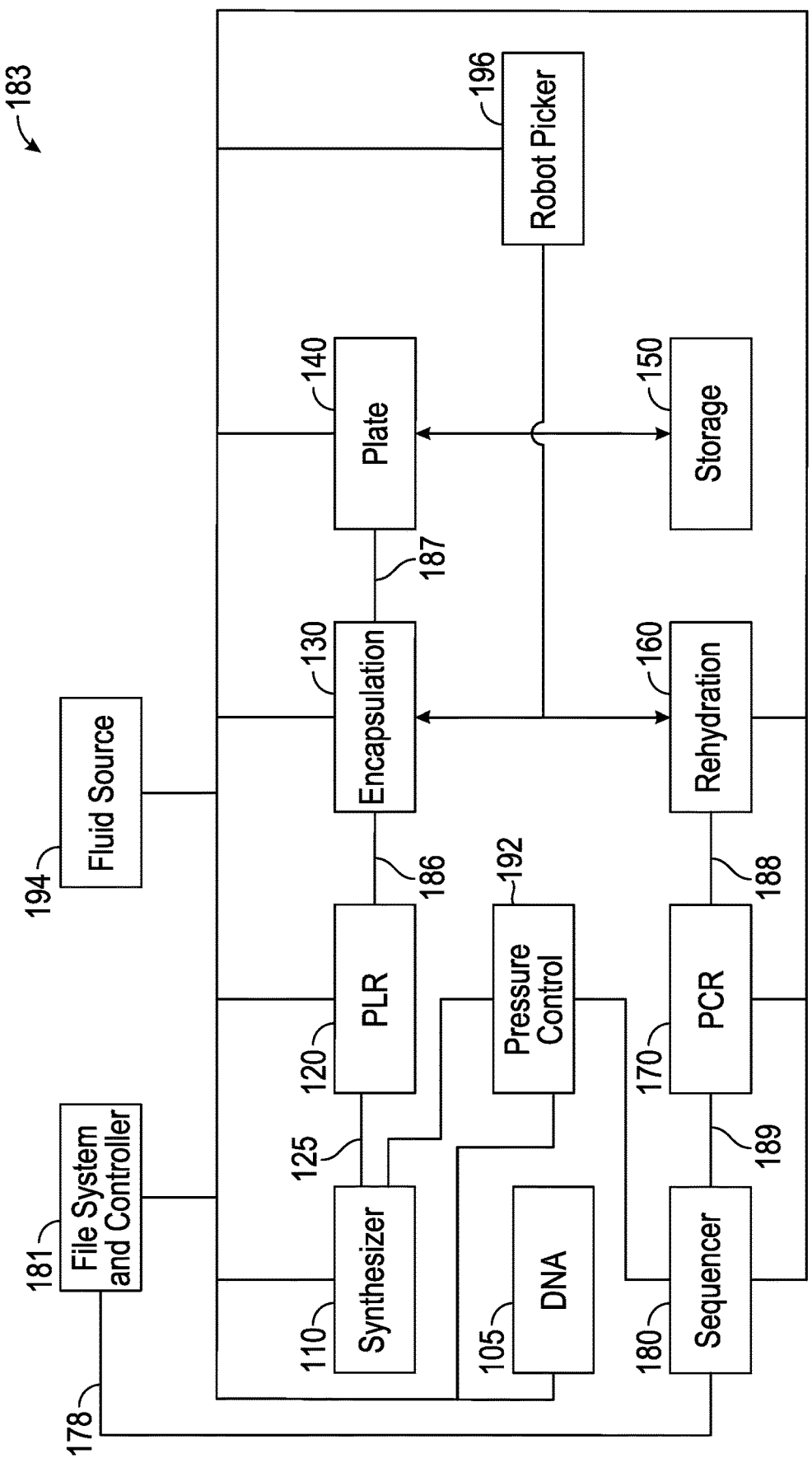
FIG. 1B is a block diagram illustrating the components of FIG. 1A, showing their connections via fluidics and robotic mechanisms for transferring DNA between the components according to an example embodiment.

FIG. 1B is a block diagram illustrating the components of FIG. 1A, showing their connections via fluidics and robotic mechanisms for transferring DNA between the components generally at 183. Reference numbers for pictorial representations of the components in FIG. 1A are also used for the same block representations in FIG. 1B. File system and controller 181 is shown with a line 178 representing a communication connection for transferring control commands to multiple components for synchronizing and controlling the components to process and transfer DNA via fluidics, also represented as lines 125, 186, 187, 188, and 189. The lines representing fluidics also represent suitable valves operating under control of file system and controller 181. A pressure module 192 is also controlled by file system and controller 181 to provide pressure variations to the synthesis module 110 and sequencing unit 180. A fluid source 194 is controlled by file system and controller 181 to provide fluids to multiple of the components via additional fluidics that are not shown for ease of illustration. Note that the fluidic connections in illustrations of the individual components show where the fluid source 194 is coupled to provide such fluids for processing. The pressure control module 192 may also provide pressure to various fluidic connections to facilitate fluid flow rates and ensure minimization of residuals. Peristaltic pumps may be used in further embodiments in addition to or in place of pressure sources. Other types of pumps may be used in further embodiments, such as syringe pumps for example. Fluid source 194 may have multiple different compartments for storing the multiple different fluids and may also include a multiplexing valve to connect the compartments to the components for delivery of the proper fluids at proper times.

A robotic picker 196, such as a robot similar to those used in semiconductor processing to move trays of wafers and chips between processing devices, is controlled by file system and controller 181 to pick and place storage plates 140 between encapsulation unit 130, storage array/library 150, and retrieval/hydration unit 160. The picker 196 may include a bar code or QR code reader to verify the proper plate is being transported to precise positions between the components so that DNA can be added to wells, removed from wells, and the plate itself can be inserted and retrieved into and from correct slots of the storage array/library 150.

Figure 2:
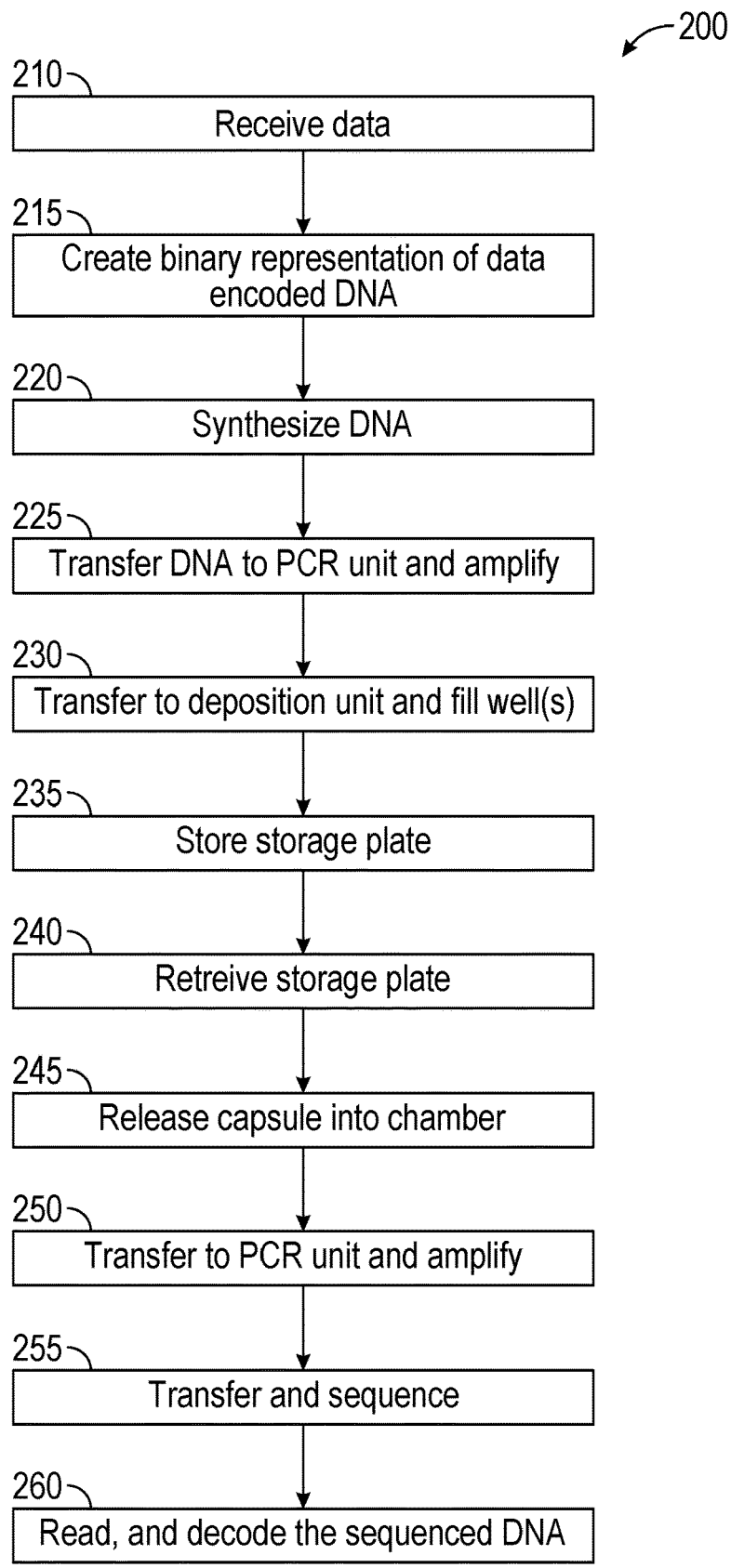
FIG. 2 is a flowchart illustration of a method for controlling the components shown in FIGS. 1A and 1B according to an example embodiment.

In one embodiment, the system 100 may be used to implement a method 200 as shown in flowchart form in FIG. 2. The method 200 may include computer-readable instructions, that when executed, control the components shown in FIGS. 1A and 1B to synthesize, store, and read DNA encoded with data.

When data to be encoded in DNA sequences is received, a data storage file system and controller 181 determines where the synthesized DNA sequences that encode the data will be physically stored and controls robots, actuators, and fluidic valves for processing, transferring, storing, and retrieving DNA at and between the various components. The controller 181 responds to commands for storing and retrieving data from the file system portion of file system and controller 181.

Method 200 begins responsive to data being received at operation 210. The received data may be binary data identifying DNA sequences that are encoded representations of data that is to be stored and retrieved or may simply be the binary data that is to be stored. If the received data is simply binary data to be stored, the data is encoded into digital representations of DNA sequences at operation 210. Error checking and/or correction codes may be included in the digital representations of DNA sequences. At operation 215, metadata received with the encoded DNA sequences are processed to determine where to physically store DNA sequences that have been processed for storage, as well as information to initiate and control the processing of the encoded DNA sequences. The metadata identifies a logical address or addresses for the data to be stored, and how to access the data by identifying one or more pairs of primers.

The encoded digital representations of DNA sequences are loaded into synthesis module 110 by operations 220, which controls the synthesis module 110 to synthesize the sequences and cleave the resulting DNA. Operations 220 may include multiple cycles of controlling valves to provide various processing fluids, such as reagents, spinning of the wafers to remove such fluids, controlling valves to provide fluid and modify pressures, as well as one or more heating cycles if desired, activating electronic actuators on the wafers and sensing conditions with on-wafer electronic/mechanical sensors. In one embodiment, a DNA oligonucleotide synthesis starts on the wafer surface, which is pre-functionalized with a linker that contains a protected or unprotected hydroxyl or amino group. The linker may also be cleavable chemically, electrochemically, photolytically, thermally, or enzymatically after the DNA synthesis is completed.

Operations 225 transfer the cleaved DNA to a flexible chemistry reaction chamber module where the DNA is amplified to make many copies of the synthesized DNA. Hundreds to millions of copies may be made in various embodiments to provide data redundancy and ensure that the original data can be retrieved. Inputs to the PCR process are the DNA, enzymes, single nucleotides, and other molecules to fuel the reaction. The reagents are thermocycled and the enzymes use the single nucleotides to make a copy of the DNA that is already there. In an ideal world, the DNA would double every cycle, but reality is not as good. Note that the PCR reagents may be replenished throughout the reaction. Operations 225 may also include the control of valves to provide various fluids, control heating and cooling, and also control actuators to open and close valves and agitate a processing chamber.

The amplified DNA is then transferred by operation 230 to a deposition unit, which is controlled to deposit the amplified DNA into one or more selected wells of the storage plate 140 that has an array of wells. The deposition unit encapsulates reacted DNA sequences by drying to remove moisture and improve storage life. A separate drying unit may be used in further embodiments to blow air or other gas across the storage plate wells. The encapsulation may be physical, or both physical and chemical in various embodiments. The DNA may be encapsulated in solution or dehydrated in various embodiments. The moisture content may be as close to 0% as possible in one embodiment, or at a level proven to lead to a long and stable storage life. In another embodiment, one or more plates with DNA may be protected from UV light. In a further embodiment, the plates 140 may be stored in a refrigerator and/or temperature and humidity controlled library or other environment.

At operation 235, the storage plate 140 may be moved by a robot into the addressable storage array/library 150 for long, or short-term storage. At operation 240, responsive to a request to retrieve the data, the robot may be controlled to retrieve a selected storage plate, such as storage plate 140, and position the storage plate 140 proximate to the retrieval/hydration unit 160. Operation 245 controls a plunger to release the DNA capsule from the well such that the capsule enters a rehydration chamber of the retrieval/hydration unit 160. Operation 245 also operates a top valve plate to provide a path for the capsule to the rehydration chamber. Various fluids are introduced to the chamber and the capsule is de-encapsulated/rehydrated as described above to result in rehydrated sequences of DNA.

At operation 250, the rehydrated DNA sequences are transferred to a further flexible chemistry reaction chamber module, which is controlled to amplify the rehydrated sequences, again by controlling multiple valves and actuators to provide fluids as well has heating and cooling, to facilitate the process as described in further detail above. In addition, preparation steps of adding more reagents, heating/cooling, shaking, etc., may also be performed. The amplified rehydrated sequences are then provided to sequencing unit 180 by operation 255 for sequencing and reading of the data-encoded DNA at operation 260. The read sequences are transferred as binary sequence data to the file system and controller 181 for decoding and providing the data responsive to the request.

The respective file system and controller portions that may be used to implement method 200 and control the components, robots and fluidics for processing the DNA may be implemented in one or more software modules and may be logically separate or integrated together in a single module in different embodiments. Tables or other types of data structures may be used to correlate logical addressees with physical storage locations of the DNA to facilitate both storage and retrieval, and to identify to the controller portion physical locations where the stored DNA resides to properly control robots for storage and retrieval. Processes may be executed by the controller to control the processing at each component as well as the transfer of DNA between the components.

Figure 3:
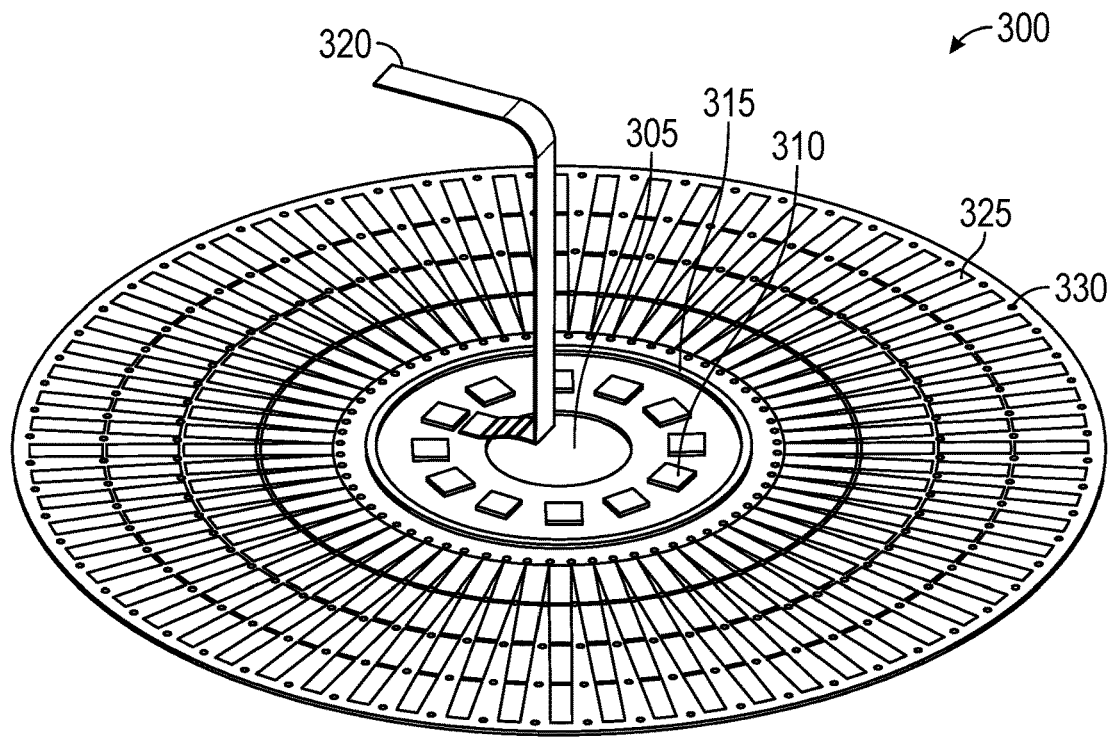
FIG. 3 is a block perspective view of a wafer for use in synthesizing and sequencing data-encoded DNA according to an example embodiment.

In one embodiment, the synthesis module 110 includes multiple wafers, such as shown at wafer 300 in FIG. 3. One example chamber 115 may include 25 wafers 300. The middle of each wafer 300 contains an opening 305, sized for mounting on a spindle or otherwise coupling a stack of wafers 300 directly to a rotating component of a motor or drive device for rotating the wafers 300. In one embodiment, the wafers may be mounted in a manner suitable for rotating the wafers up to approximately 1000 rotations per minute (rpm) or higher, suitable for using centrifugal force to remove fluids from the wafers. The number of rpms may be varied depending on the characteristics of the fluids. Fluids with a higher viscosity may be removed using higher rpms than fluids with lower viscosity. Fluids may be distributed about the wafers via rotations at lower rpms, such as rpms suitable for distributing fluids. In one embodiment, a medium to high vacuum may be used to ensure introduced fluids occupy the voids within the chamber.

The wafers may be in the shape of a circle or disk. In one embodiment, the wafers are 1.0 mm thick, with a diameter of 300 mm. Control electronics 310 may be supported by the wafer 300 and dispersed in a circular pattern radially spaced from opening 305. The control electronics 310 may be positioned between the opening 305 and a circular gasket 315, which may extend around the wafer 300 in a circle or other desired shape such that when multiple wafers 300 are stacked, the respective gaskets 315 of each wafer 300 mate and form a seal to insulate the electronics from the rest of the chamber. The seal via the gaskets 315 prevents processing fluids from reaching the electronics. The gaskets 315 may also serve to hold the wafers 300 in place during rotation by the rotating component. In one embodiment, the opening 305 may be potted by simply filling the opening 305 with epoxy, which also serves to bond the wafers 300 in the stack together.

A flex cable 320 or flex circuit 321 may be electrically coupled to the control electronics 310, which may include memory chips, for data transfer to and from the control electronics 310 from and to circuitry external to the wafer 300. In some embodiments the control electronics 310 may communicate wirelessly via transceivers built into the control electronics 310. Inductive power coupling may be used for powering the control electronics 310, and wireless or optical communication means may be used depending on desired data transfer rates. Power for the control electronics 310 may be provided via the flex cable 320, batteries coupled to the control electronics 310, or via electromagnetic or motion-based transducers coupled to the control electronics 310, obviating the need for physical electrical connection.

A plurality of reticles 325 may be dispersed in an efficient pattern about the wafer 300, extending radially from the gasket 315. The reticles 325 may be positioned on or otherwise supported by the wafer 300, such as a silicon wafer in one embodiment, and serve to hold fluid and DNA during synthesis, serving as the processing sites for data encoded DNA manufacturing. In one embodiment, there are four concentric circles of reticles 325 extending outward from the gasket 315. Standoff wafer pitch fiducials 330 may be formed between the reticles 325 in concentric circles about the radial edges of the reticles 325 as shown in FIG. 3. The fiducials 330 may be etched or otherwise formed on or in the wafer 300 and serve as visual markers for imaging and/or otherwise detecting positions of the reticles 325 on the wafer 300. In one embodiment, the fiducials 330 may be used for gap control. With accurate fiducial height, the fiducials 330 may also be used to minimize a gap tolerance between wafers 300 in the stack.

In one embodiment, the reticles 325 may be functionalized with a linker that contains a protected or unprotected hydroxyl or amino group to aid in DNA synthesis. Reticles control growth of the DNA sequences via a variety of methods including optical, electrochemical, thermal, or microfluidic deposition methods. The input to the synthesis module 110 is a digital description of desired DNA sequences, while the output is molecules with DNA sequences that encode information for storage.

Large-scale DNA manufacturing is challenging due to the level of automation and delivery/evacuation of chemical reagents to surfaces where the DNA is grown. The stacked assembly of DNA synthesis wafers that are rotatably mounted and supported aids in centrifuging reagents out of the space between the wafers. The rotatable stack, coupled with pressure control creation in the chamber, provides for complete evacuation of used reagents and admission and filling of new reagents in the chamber.

For DNA synthesis, the wafers may be exposed to reagents in series, interspersed with activation of elements on the wafers (light sources for optical control, electrodes for pH-based or thermal-based electronic control, and throttles for mechanical control). For DNA synthesis, a UV spectrometer or other method may be used to measure DNA concentration. The reagent delivery and evacuation are challenging for a stack of wafers.

The stack of wafers in one embodiment are enclosed in the chamber 115. A vacuum may be used to completely fill the chamber 115 with one reagent at a time. First, the chamber is emptied by spinning the wafers and applying a positive pressure. A vacuum is then created and a valve is opened that lets the selected reagent in, completely filling the empty spaces in the chamber. Next, if needed, active elements in the wafer are activated. Finally, pressure is used again to evacuate the reagent from the chamber, leaving it ready for the next step/reagent.

Cleavage and deprotection of the DNA may be done in the chamber, either via pressurized gas injection, or a solution that is then heated (or a combination thereof). The selection of reagents entering and exiting the chamber is done via a configurable valve system. Multiple synthesis modules 110 having chambers with stacks of wafers may be mounted on a rack in one embodiment for mass production. The rack may be located in a data center, using mechanical structures commonly used for mounting conventional computing and data storage resources in rack units having openings adapted to support disk drives, processing blades, and other computer equipment.

Figure 4A:
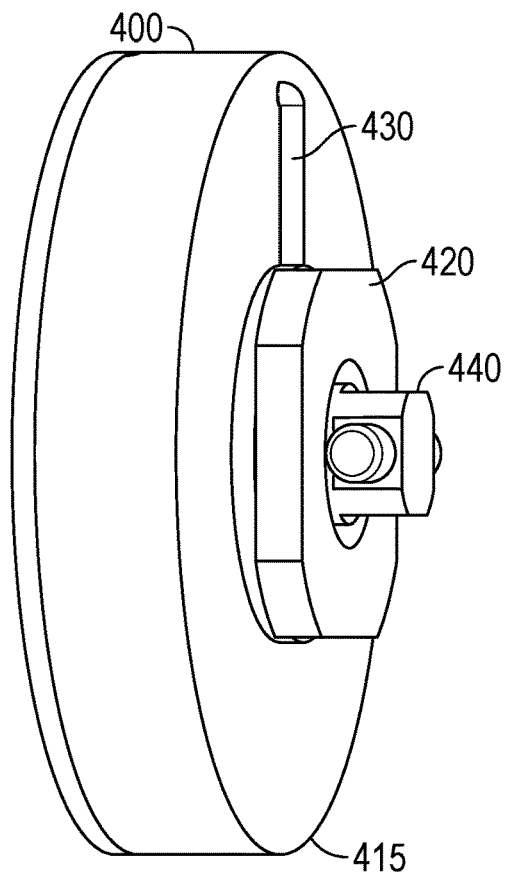
FIG. 4A is a perspective view of a synthesis module unit according to an example embodiment.
Figure 4B:
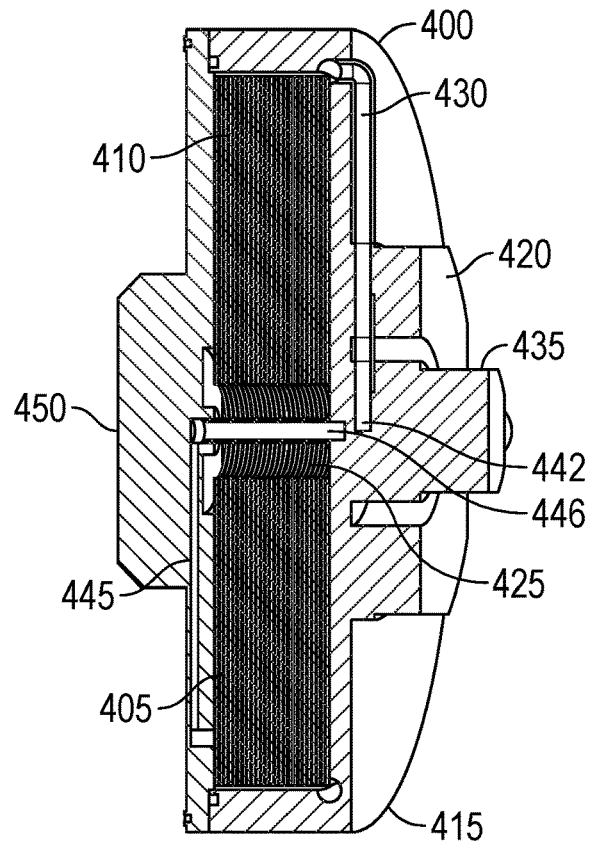
FIG. 4B is a cut-away perspective view of the synthesis module unit according to an example embodiment.

FIG. 4A is a perspective view of a synthesis module unit 400. FIG. 4B is a cut-away perspective view of the synthesis module unit 400 showing a chamber 405 in which a stack 410 of 25 rotatably mounted wafers is disposed. The synthesis module unit 400 has an outer shell 415 that is coupled to the wafer stack 410 and rotates with the wafer stack 410 and chamber 405 in one embodiment.

A rotary servo drive 420 is coupled to the wafer stack 410 and functions to rotate the wafer stack 410. The drive 420 may be similar to a disk drive rotary servo drive and may be controlled via control electronics 310 or external control electronics. An internal dry column 425 provides a dry environment for electronics 310 and the flex cable 320.

Fluid may be provided to the wafer stack via a liquid fill/drain line 430. Line 430 in one embodiment extends radially from a dual port liquid/gas rotary swivel 435 that aligns with the line 430 responsive to the wafers not rotating and being properly aligned with line 430. Line 430 opens to the chamber 405 near the periphery of the wafer stack. The swivel 435 is also static in one embodiment and contains two-way solenoid valves 440 that operate to controllably open and close to provide access to the line 430 via a fluid fill port 442 for adding fluid to the wafers via the fluid fill port 442 and for draining fluid from the wafers. Other configurations of line 430 may be used in further embodiments that serve to provide and evacuate fluid from the chamber 405. Orientation of the chamber 405 may be controlled to facilitate draining of fluid in some embodiments, in addition to the use of centrifugal force. Locating the opening of line 430 proximate the periphery of the wafers, and/or chamber 405 itself, may serve to better drain fluid.

The valves 440 also operate to utilize a gas vacuum/pressure line 445 via a fluid purge port 446 to controllably increase and reduce pressure in the chamber 405 in which the wafers rotate. The line 445 in one embodiment extends from the valves 440 through the dry column 425 and extends radially outward toward the outer edges or periphery of the wafers, opening into chamber 405. Other configurations may be used to control the pressure of gas in chamber 405.

In one embodiment, synthesis electronics 450 control a synthesis process, including fluidic controls and rotational controls, as well as other process parameters commonly utilized in DNA synthesis. The synthesis electronics 450 may also rotate with the outer shell 415 and wafer stack 410. Synthesis electronics 450 may include controller 181 or be in communication with controller 181. The control functions for synthesis module unit 400 may also be distributed between the one or more controllers in various embodiments.

Synthesis may be performed using known processes and in particular by using synthesis module unit 400. Processing fluids may be added to and drained from the chamber 405 in succession. To inject fluids in the chamber, a light vacuum may be pulled via line 430 from the fluid purge port 446, and the fluid admission port 442 coupled to line 430 is opened via the valves 440. To drain fluids from the chamber 405, positive pressure in the chamber 405 in conjunction with centrifuging the wafer stack 410 to drain fluids at the fluid purge port 446. The fluid volume of the chamber may be on the order of 1 liter but may vary significantly depending on the scale of the module unit 400 and gap between wafers. The DNA in the reticles 325 of the wafers is deprotected and cleaved by filling the chamber 405 with cleavage/deprotection reagents and heating up the chamber 405 for a few hours. The entire synthesis module unit 400 may be heated (and optionally subjected to higher than atmospheric pressure) by an external heat source in some embodiments, or by optional heating elements thermally coupled to the chamber 405.

Following synthesis via synthesis module unit 400, the fluids from the synthesis, referred to as DNA solution, are drained via port 442 and transported by fluidic structures, such as tubes, to retrieval/hydration unit 160. A flexible chemistry reaction chamber module 500 is shown in further detail in FIG. 5.

The fluidic structures from port 442 couple to flexible chemistry reaction chamber module 500 at a tube 510 and provide the DNA solution to an optional filter 515 layer. The filter 515 layer in one embodiment may be a glass fiber membrane, an anion exchange filter unit, or another solid phase extraction filter unit to capture synthesized DNA to a passage 518 of filter material, with solvent, salts, and other small molecule impurities flowing to recycling or waste. Another buffer solution is used to elute the DNA into a flexible chemistry reaction chamber 520 (whose volume is about 10 milliliters in one embodiment), and additional reagents for the PCR or other processing are added at this point. Hot liquid may be circulated in a fluidic thermal loop 525 around the chamber to thermocycle the DNA and reagents. An optional heating element 528 may be thermally coupled for effecting rapid changes in DNA fluid temperatures in the flexible chemistry reaction chamber 520. Once the PCR or other processing completes, the resulting DNA containing fluid may be cleaned up by a filter similar to filter 515. Note that PCR may be used to amplify correct sized DNA.

The flexible chemistry reaction chamber module 500 may include a top layer 530 that is coupled to tube 510 to receive the DNA solution from the synthesis module unit 400. The top layer 530 contains a first passage 538 that is aligned with passage 518 of filter material to allow filtered DNA solution into chamber 520.

A first linear actuator 545 is coupled to a bottom valve layer 550 having an exit opening 552. The first linear actuator 545 may be used to provide a valve function for the chamber 520. As shown, the valve is open, allowing DNA solution to exit the flexible chemistry reaction chamber module 500 via a fluidic tube 555. The first linear actuator 545 may controllably move the bottom valve layer 550 laterally to close the valve by making sure the exit opening 552 is not overlapping with the chamber 520. The surfaces of each adjacent layer may be polished to provide a fluid-tight seal when contact is maintained. Mating hardened, flat, polished surfaces of the layers provides for a fluidic seal. Ceramic, carbide, and diamond like coatings may be used to provide such surfaces.

A second linear actuator 560 is coupled to a chamber layer 565 disposed between the filter 515 layer and the bottom valve layer 550. The adjacent surfaces of each layer are also hardened, flat, and polished to provide a liquid seal. Second linear actuator 560 may be used to agitate the chamber 520 in a manner conducive to mixing reagents used for the PCR reaction. Note that the use of hardened, flat, polished surfaces provides for low friction lateral movement and also vertical retentive force, as it is very difficult to vertically separate hardened polished surfaces in contact with each other. Thus, the various layers of the flexible chemistry reaction chamber module 500 stay coupled absent a significant external vertical force applied to them. In some embodiments, the layers may be disposed or otherwise supported in a container that provides some vertical force, as well as a horizontal force to at least one non-moving layer such that the actuators only move one layer at a time in a controlled manner, as controlled by the electronics module, such as electronics 310, or an external electronics module.

The container may provide support for the actuators, which may be used to support the layers and lock the layers in position when not moving the respective layers. The actuators 545, 560 have an actuator element, such as rods 570 and 575, that contacts the respective layers and laterally moves into and out of the actuators 545, 560 as indicated by double arrow lines 580, 585. Magnets or electromagnets may be used for DNA manipulation in various embodiments.

Once the PCR completes, the DNA may be cleaned up by a filter similar to filter 515 layer and passage 518 of filter material. The filtered DNA is deposited in 20 different wells (or a different arbitrary number) of a high-density physical storage plate, along with materials to encapsulate the DNA for long-term physical storage.

Figure 6A:
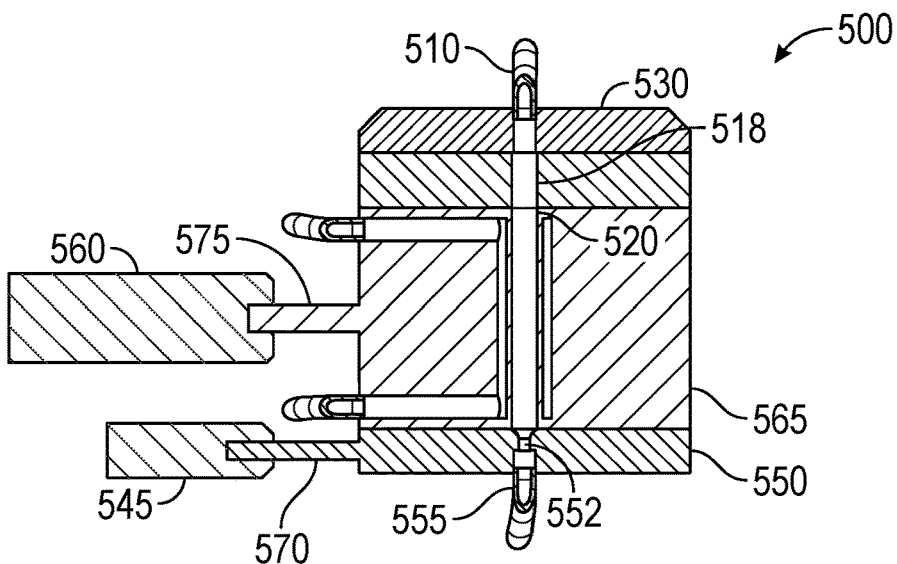
FIGS. 6A, 6B, and 6C are block cross sections of the flexible chemistry reaction chamber module illustrating different positions of layers during data-encoded DNA processing creating different flexible chemistry reaction chamber module states according to an example embodiment.
Figure 6B:
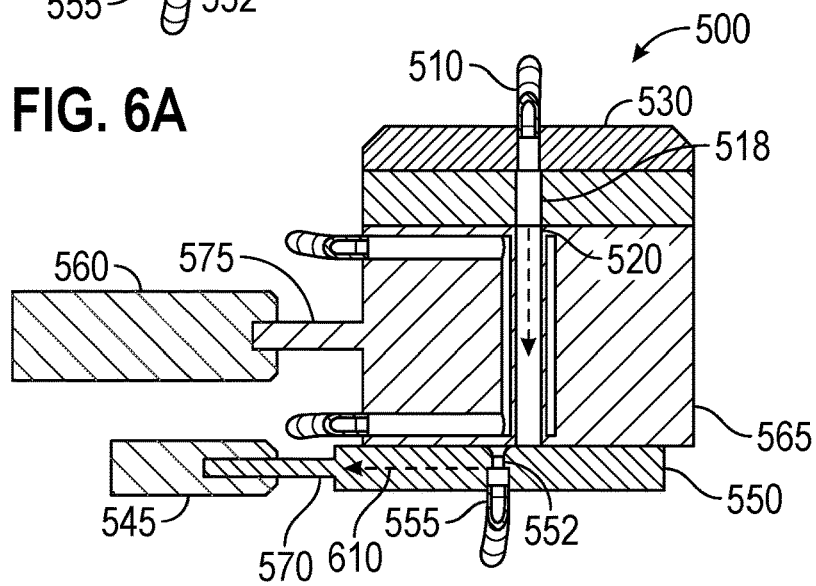
Figure 6C:
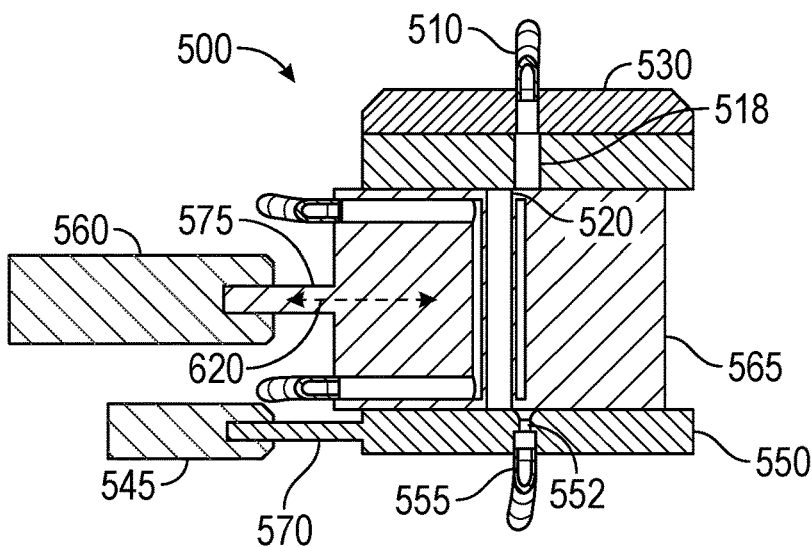

FIGS. 6A, 6B, and 6C are block cross sections of the flexible chemistry reaction chamber module 500 illustrating different positions of layers during data-encoded DNA processing creating different flexible chemistry reaction chamber module states. FIG. 6A shows flexible chemistry reaction chamber module 500 with the actuators 560 and 545 positioning the tube 510, flexible chemistry reaction chamber 520, and exit opening 552 in-line. In the illustrated state, a fluid passthrough state, elution of the amplified DNA solution out of tube 555 may occur. At different times, such as between amplifying different DNA, the same state of the flexible chemistry reaction chamber module 500 may be used to remove fluids and leftover DNA or other material in preparation for amplifying the next batch of DNA.

FIG. 6B illustrates a state of flexible chemistry reaction chamber module 500 where the first actuator 545 has moved the bottom valve layer such that the exit opening 552 is blocked by a polished flat surface of the bottom valve layer 550. The direction moved is shown by arrow 610. Such state, referred to as a fluid adding state, may be used to add fluids containing DNA and other reagents or processing fluids as desired for amplifying the DNA.

FIG. 6C illustrates the use of the second actuator 560 to agitate or otherwise move the chamber layer transverse to the axis of the flexible chemistry reaction chamber 520, while maintaining a closed flexible chemistry reaction chamber 520 as illustrated by arrow 620. The state illustrated in FIG. 6C may be referred to as a closed, or processing state. In one embodiment, the range of motion of the chamber layer 565 is controlled such that agitation may be performed without overlapping either the exit opening 552 or the tube 510. While the flexible chemistry reaction chamber 520 is shown to the left of the opening 552 and tube 510, agitation may alternatively be performed with the chamber 520 on the right side. Both ends of the flexible chemistry reaction chamber 520 abut polished surfaces of the top layer 530 and bottom valve layer 550 during such agitation, trapping fluids in the chamber 520 for processing. Following amplification, the fluid passthrough state shown in FIG. 6A may be used to elute the DNA solution from the flexible chemistry reaction chamber 520.

Figure 7:
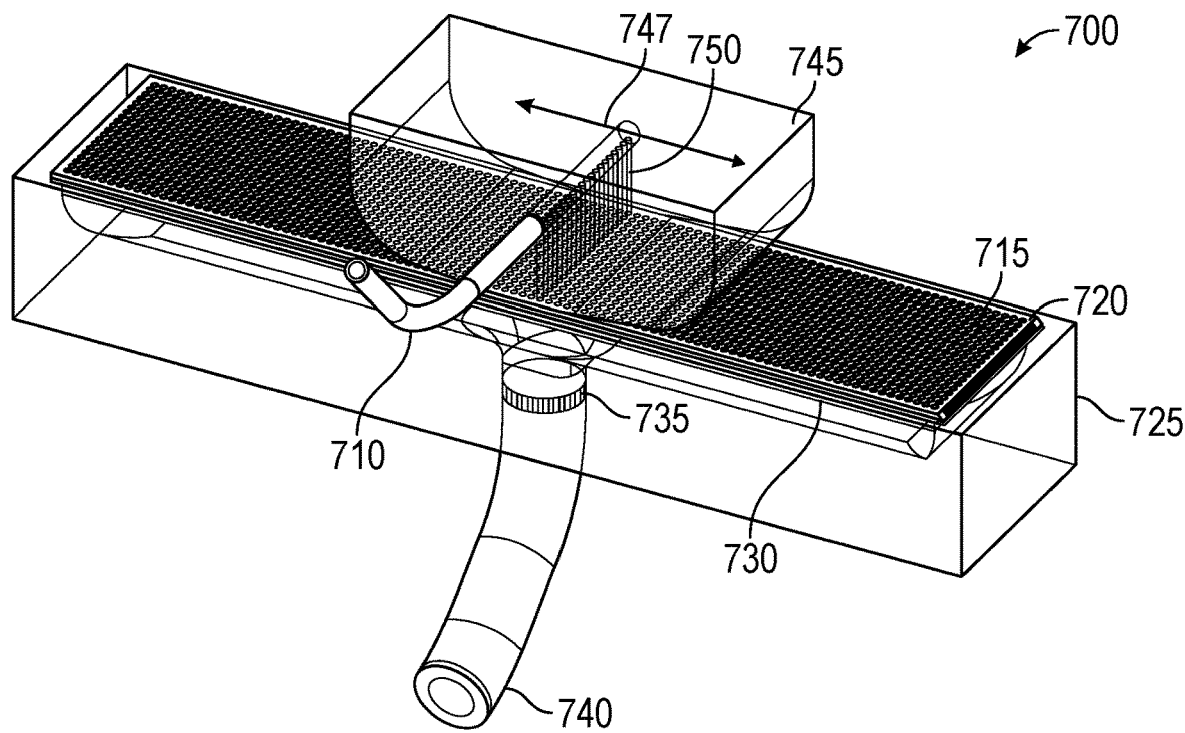
FIG. 7 is a perspective illustration of devices involved in depositing the DNA according to an example embodiment.

FIG. 7 is a perspective illustration of devices 700 involved in depositing the DNA generally. A tube 710 is used to transport the filtered DNA into wells 715 of a storage plate 720. The storage plate 720 is supported by a filling fixture 725 that supports the plate 720 in a recess 730. The recess 730 has a drain 735 coupled to a drain tube 740 for removing excess fluid and DNA.

The filtered DNA is provided via tube 710 to a fill head 745 that is moved laterally, as indicated by arrows 747, along the storage plate 720 to fill the wells 715. A film or membrane may be provided on a side of the storage plate 720 opposite the side from being filled via fill head 745. The film should be sufficient to protect the resulting capsules of DNA from moisture and preserve the DNA for long periods of time. Example materials for the film may include aluminum, gold, other metals, polymers, silica oxide, inorganic salts and sugars, thin film glass, thin polymers like EPDM, Kapton, polypropylene, and other non-porous materials suitable for protecting the DNA and also removable for accessing the DNA. The film in some embodiments may be releasable to allow access to the DNA during later retrieval and rehydration. In some embodiments, no film is needed, as the wells may be sized such that capillary action and surface tension will keep fluid in the wells. However, in other embodiments, the films may provide hermetic seals to keep capsules and inert gas in a sealed environment to minimize DNA degradation over long periods of time.

The fill head 745 in one embodiment has multiple fill tubes 750 coupled to tube 710 arranged in a line transverse to the direction of lateral movement of the fill head 745. The multiple fill tubes 750 are positioned above the wells 715 such that fluid eluted from the fill tubes 750 fills selected wells 715. In further embodiments, the fill tubes 750 may be positioned close to the wells 715 such that capillary action fills the wells 715 regardless of the orientation of the devices 700.

The fill head 745 may include one fill tube 750 per column of wells 715, such that one pass of the fill head 745 laterally along the columns may fill all of the wells 715 in the array of wells. Multiple passes may be performed in further embodiments to ensure complete or a desired amount of filling. The fill tubes 750 may also include valves to precisely control which wells 715 receive DNA during each pass, such that different data-encoded DNA may be placed in selectable wells on an individual basis. The valves may be controlled by one or more controllers previously referenced. In one example, one or more columns may receive the same data-encoded DNA, while one or more other columns may receive different or multiple different sets of data-encoded DNA. Further, rows of wells or even individual wells 715 may be selected for a set of data-encoded DNA. The file system and controller 181 may generate an address identifying the physical location of each well 715 or sequence of wells containing DNA encoded with selected data, and then control the fill tubes 750 during each pass to fill the identified wells 715.

Following filling, the plate 720 may be heated to facilitate drying of the DNA solution in the wells 715. In one embodiment, as much moisture as possible may be removed from the resulting capsules of DNA. A film may be used to cover the DNA in the wells 715 when dried.

In various embodiments, standard robotic equipment may be used to move the storage plate 720 into and out of the filling fixture 725, and to move the fill head 745 as desired laterally across the storage plate 720 under control of one or more controllers.

Figure 8:
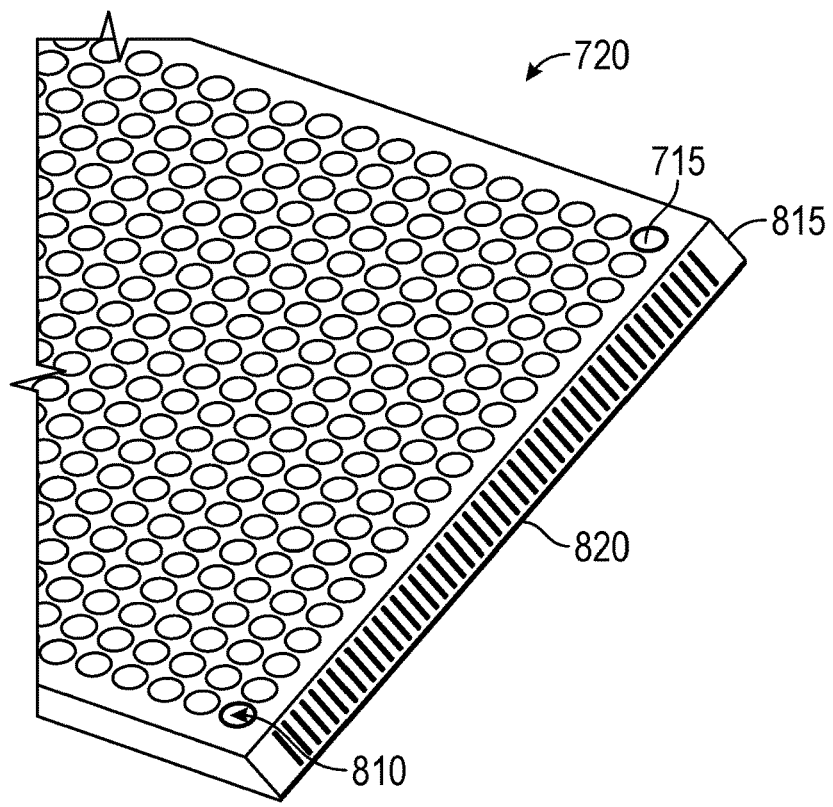
FIG. 8 is a partial perspective representation of a storage plate having an array of wells or spots according to an example embodiment.

FIG. 8 is a partial perspective representation of storage plate 720 showing wells 715 in further detail. A row 810 of 20 wells is indicated at an end 815 of the storage plate 720. Rows may have more or fewer wells 715 in further embodiments, and the size of a well 715 may also vary depending on the amount of DNA desired to be stored. End 815 in one embodiment may include encoded markings, such as a bar code 820. The bar code 820 may be encoded with a unique identifier for the plate 720, which may be scanned to confirm that the plate 720 is the correct plate during various storage and retrieval operations.

Figure 9A:
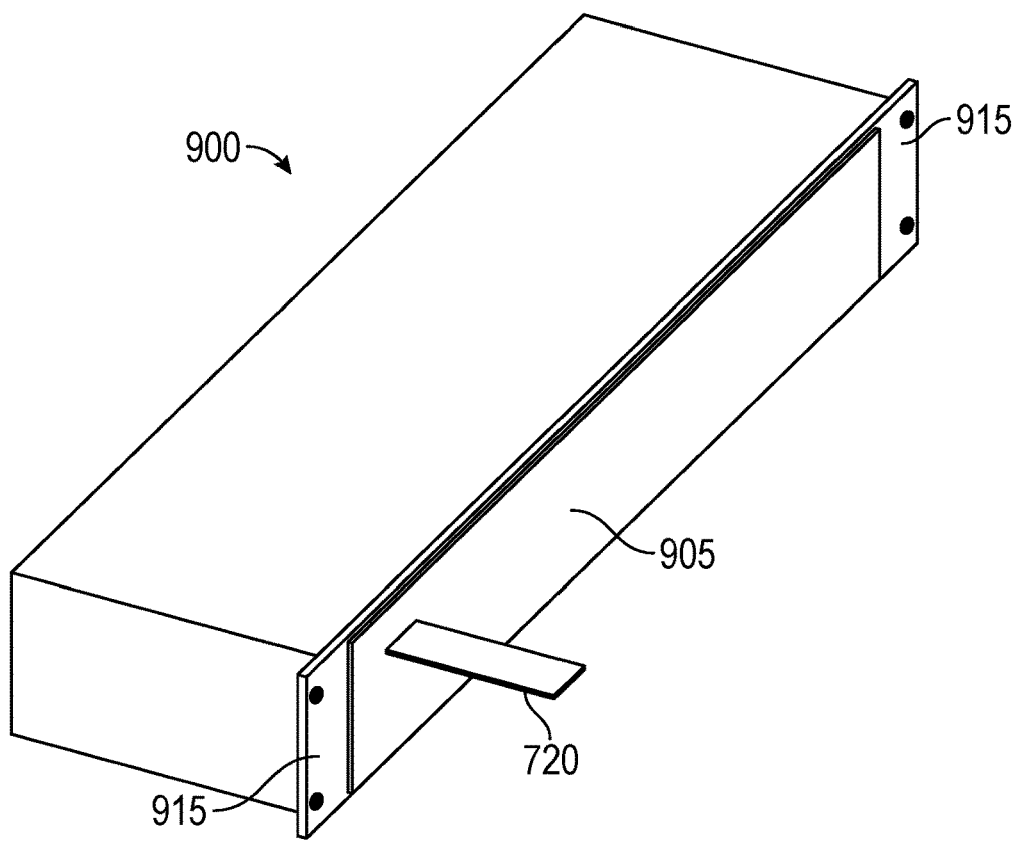
FIG. 9A is a block perspective view of a storage library with a storage plate positioned proximate a slot according to an example embodiment.

The storage plate 720 may be moved into a slot of physical storage array/library 900 as illustrated in a perspective representation in FIG. 9A. A robot may be used to insert one or more storage plates 720 into selected slots 905 of the storage library 900. In one embodiment, the storage library 900 may have multiple slots, and include one or more flanges 915 or other mechanism or means to couple the storage library 900 to an equipment rack. Each slot 905 may have a physical location and logical address that the file system may use to control the robot to identify the proper slot 905 for each plate. Note that the slots 905 are arranged as an array on an open side of the storage library 900 to provide a three-dimensional storage space accessible by the robot from the open side. The bar code 820 may alternatively be used to identify the plate or to confirm that the correct plate was stored in the correct slot. Storage plate 720 is shown proximate a slot of the storage library 900 and illustrates either insertion into or retrieval from the storage library 900.

Figure 9B:
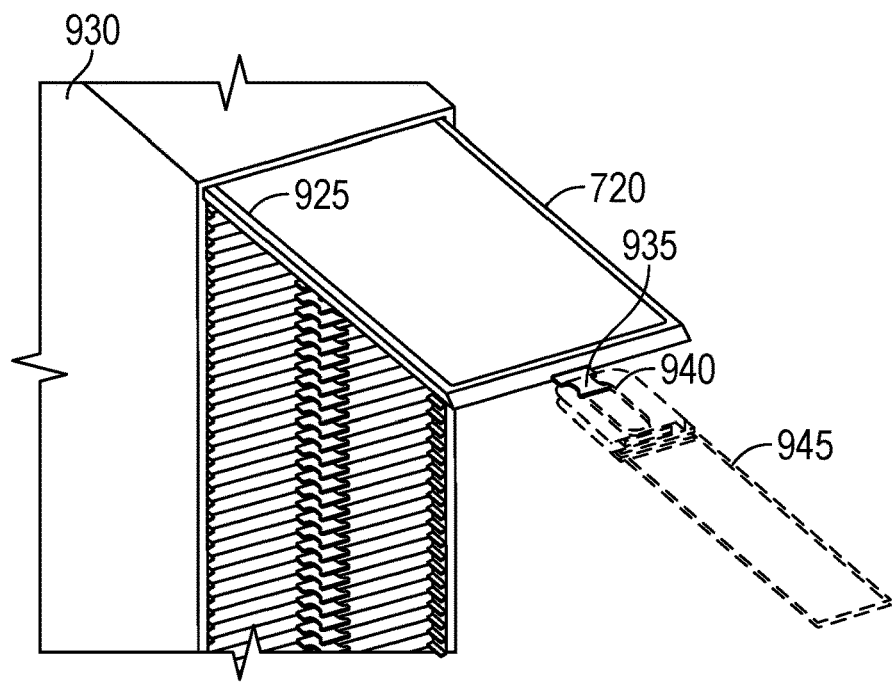
FIG. 9B is a perspective view illustrating a storage plate partially inserted into a slot of a storage library according to an example embodiment.

FIG. 9B is a perspective view illustrating a storage plate 720 partially inserted into a drawer or slot 925 of a storage library 930 having an arrangement of multiple vertically stacked adjacent slots. Storage plate 720 has a transport protrusion 935 coupled to an end of the storage plate 720. The transport protrusion 935 may be shaped to mate with two opposed robot arm protrusions 940 supported by a moveable robot arm 945. The two opposed robot arm protrusions 940 may be shaped to releasably engage the transport protrusion 935, allowing the robot arm 945 to move the storage plate 920 into and out of one of the storage library 930 slots.

Figure 9C:
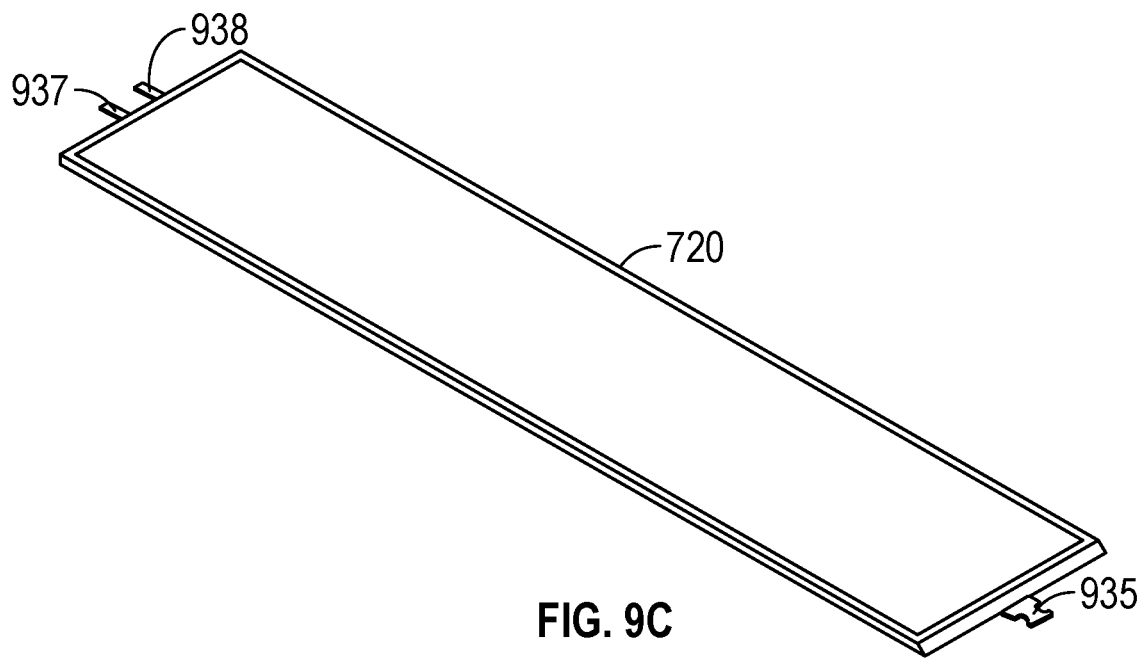
FIG. 9C is a perspective view of a storage plate according to an example embodiment.

FIG. 9C is a perspective view of storage plate 720 showing further detail of the transport protrusion 935. In one embodiment, the transport protrusion 935 is a plate that is coupled on one end to the storage plate 720, optionally tapering for a distance away from the storage plate 720, and then having an enlarged portion on a distal end of the transport protrusion 935 suitable for engaging with the opposed robot arm protrusions 940. Many different shapes of the mating protrusions may be used in further embodiments.

Figure 9D:
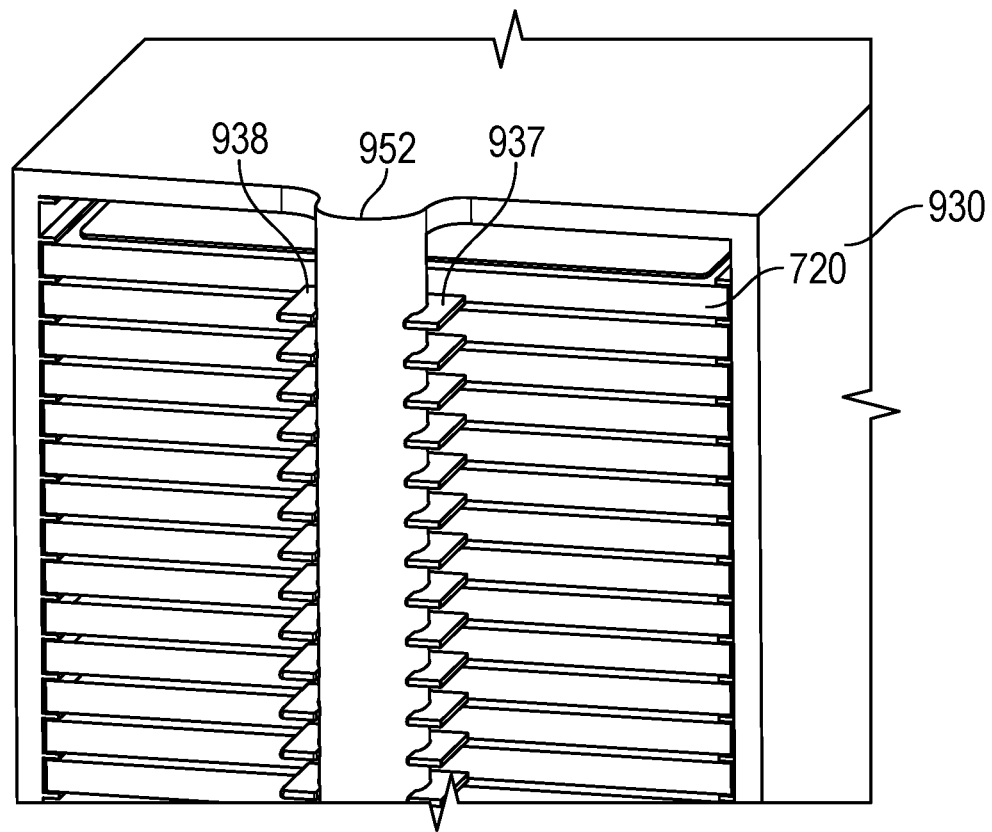
FIG. 9D is a perspective view of a back of the storage library according to an example embodiment.

On an opposite end of the storage plate 720, a pair of opposing retention protrusions 937 and 938 may be formed. The opposing retention protrusions 937 and 938 may be used to engage a retention post 952 formed on a back of the storage library 930 as shown in a perspective view in FIG. 9D of a back of the storage library 930. The opposing retention protrusions 937, 938 may have a suitable spring constant to securely hold the storage plate 920 when fully inserted into the slot when the protrusions 937, 938 are engaged with the retention post 952. The spring constant may be small enough to allow release of the storage plate 720 with a force compatible with both the retentive force of the robot arm protrusions 940 to allow insertion and removal of the plates.

Figure 9E:
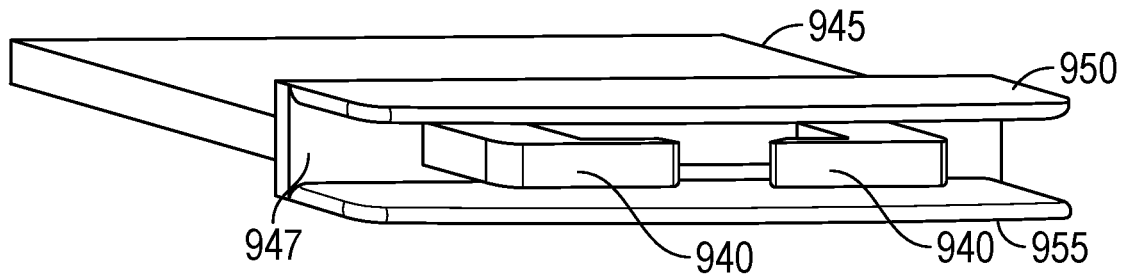
FIG. 9E is a perspective view of a robot arm protrusion according to an example embodiment.

The robot arm protrusions 940, shown in further detail in perspective view in FIG. 9E, should be formed to provide suitable support for the storage plate 720 as well as sufficient retentive force to ensure the storage plate 720 is retained during transport. Robot arm protrusions 940 may be formed with distal portions that extend toward each other to mate with the enlarged portions of the transport protrusion 935. The opposed robot arm protrusions 940 may be formed to releasably engage the storage plate protrusions 937, 938, such as by use of actuators or piezo electric materials to control a distance between the opposed robot arm protrusions 940 that mate with the enlarged portion of the transport protrusion 935.

FIG. 9E is a perspective view showing further detail of a storage plate engagement portion 947 of the robot arm 945. The storage plate engagement portion 947 includes the opposed robot arm protrusions 940 sandwiched between two support plates 950 and 955. The support plates 950 and 955 help support the storage plate 720 when engaged with the robot arm protrusions 940, limiting vertical movement of the storage plate 720 during transport, insertion into the storage library 930, and picking and placing in various other equipment used for processing and handling the storage plates and DNA.

Figure 10:
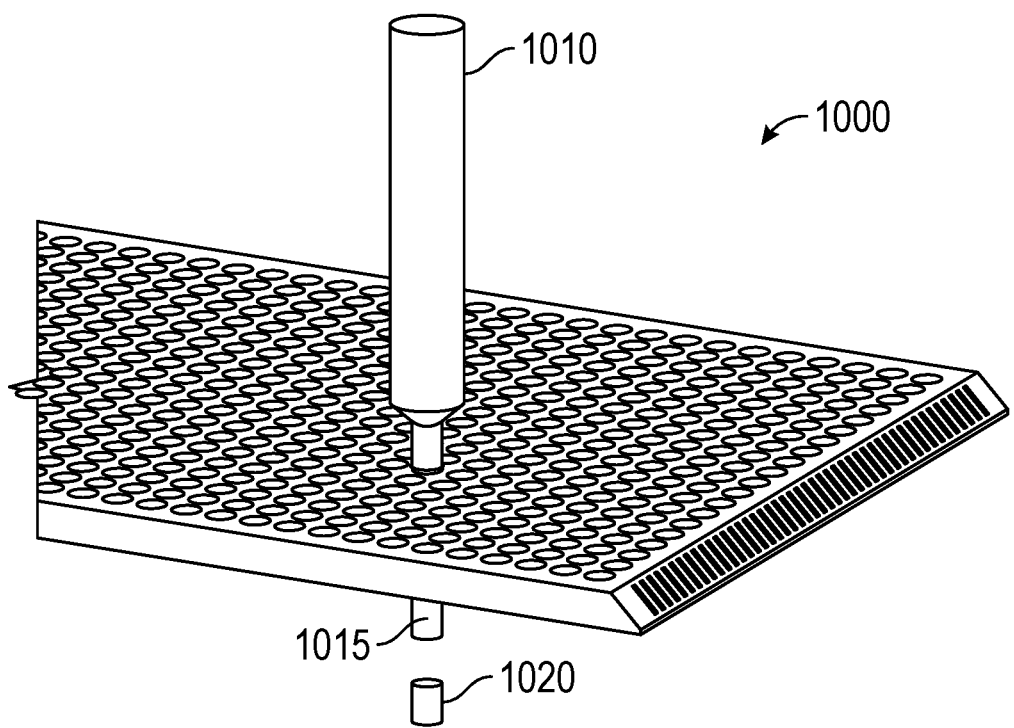
FIG. 10 is a block perspective view of a plunger removing a capsule of DNA from a storage plate well according to an example embodiment.

To retrieve the DNA, the physical storage plate 720 is retrieved from the library 900. One (or more) of the capsules is pressed out of the physical storage plate 720 as illustrated in FIG. 10 at 1000. A plunger 1010 has a portion 1015 sized to fit in a well and move a capsule 1020 of DNA through and out of the well in which it is stored. The plunger 1010 may be coupled to or used by the robot picker 196 to remove the capsule from the well. Retrieval of DNA from spots may be performed by electrowetting via a microfluidic platform configured to provide fluid to each desired spot.

Figure 11A:
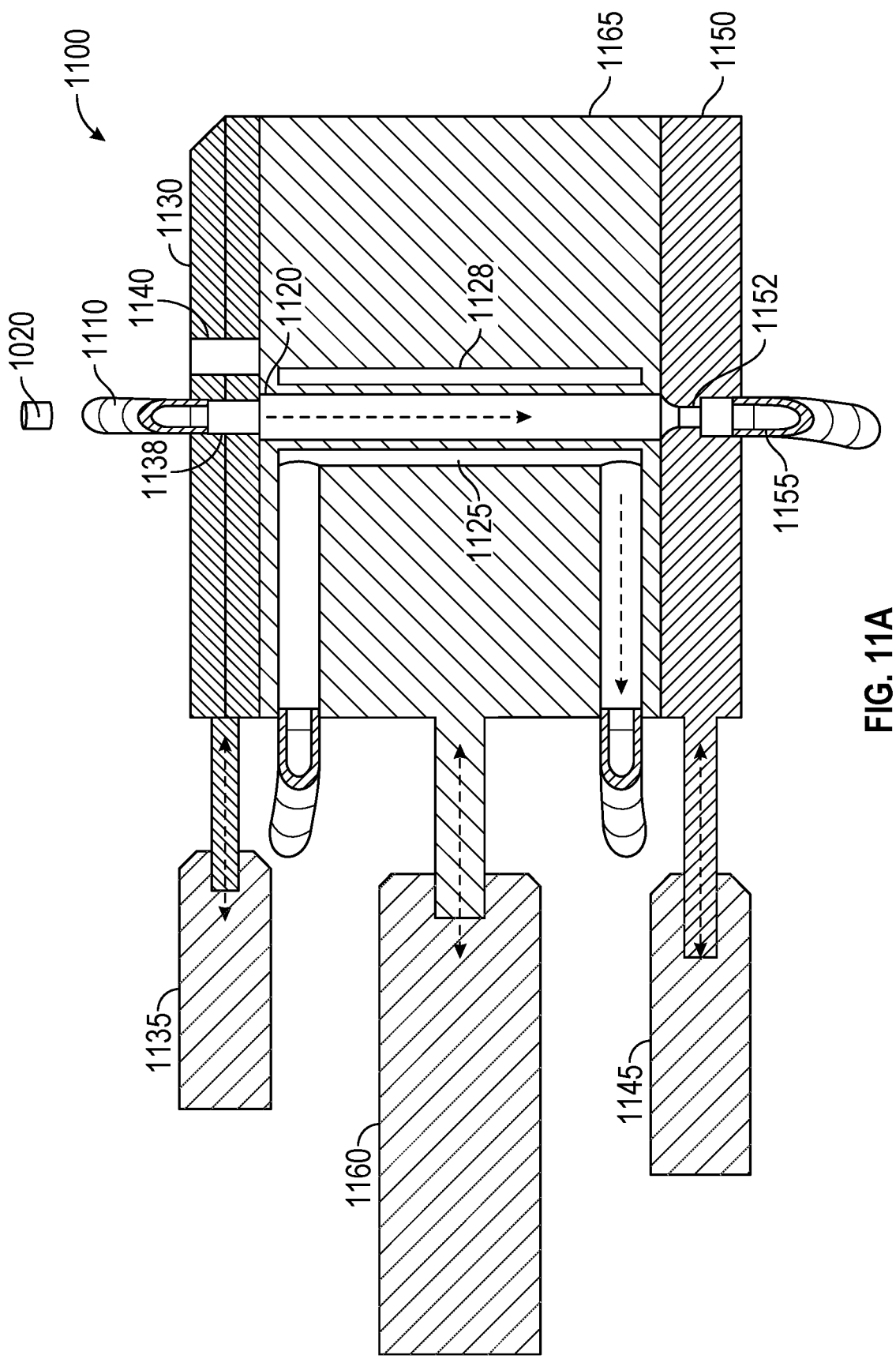
FIG. 11A is a block cross section of a rehydration unit according to an example embodiment.

The capsule 1020 is then provided to a rehydration unit 1100 shown in a block cross section view in FIG. 11A. Rehydration unit 1100 is very similar to flexible chemistry reaction chamber module 500, with the addition of a third linear actuator 1135 coupled to a top valve layer 1130. The top valve layer 1130 has an additional opening 1140 to receive the capsule 1020 and provide the capsule 1020 to a chamber 1120 where new fluids are added and agitated to dissolve the capsule 1020 and rehydrate the DNA.

Figure 11B:
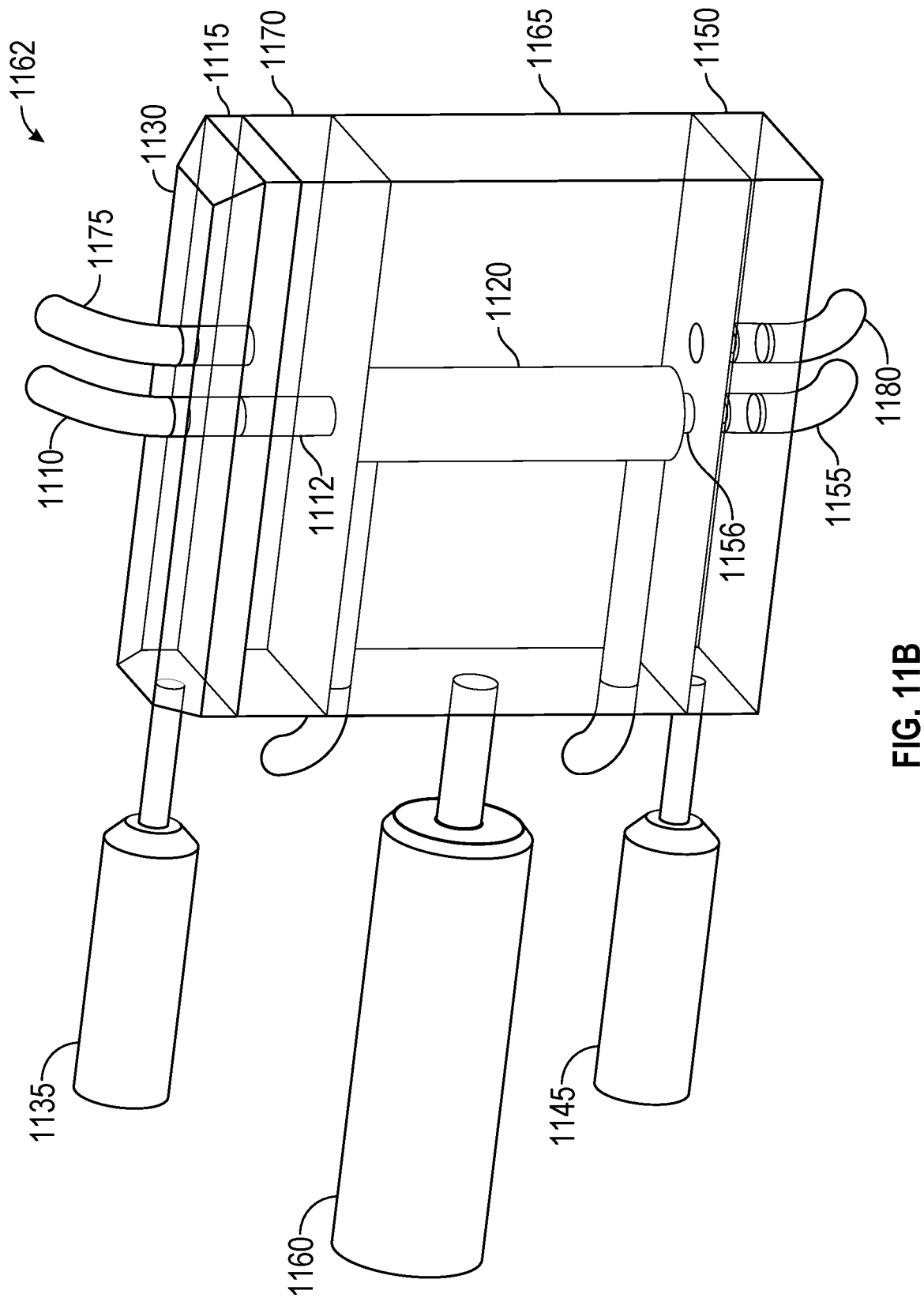
FIG. 11B is a semi-transparent perspective view of a combined reaction chamber and rehydration module according to an example embodiment.

The fluidic structures couple to rehydration unit 1100 at a tube 1110 and provide rehydration solutions to the chamber 1120 containing the capsule 1020. Hot liquid may be circulated in a fluidic thermal loop 1125 around the chamber 1120 to thermocycle the DNA and solutions. An optional heating element 1128 may be thermally coupled for effecting rapid changes in DNA fluid temperatures in the chamber 1120. Once the rehydration completes, the resulting DNA-containing fluid may cleaned up by a filter (similar to filter layer 1170 as shown in FIG. 11B).

Still referring to FIG. 11A, rehydration unit 1100 may include the top valve layer 1130 that is coupled to tube 1110 to receive various solutions for rehydrating the capsule 1020. The top valve layer 1130 is coupled to the third linear actuator 1135 that operates to move the top valve layer 1130 laterally with respect to a chamber layer 1165. The mating surfaces of each may be polished to provide a fluid-tight seal when contact is maintained. The top valve layer 1130 contains a first passage 1138 that is alignable with the chamber 1120 for receiving rehydration fluids. An additional opening 1140, laterally spaced from first passage 1138, may be controllably positioned via the third linear actuator 1135 to accept the DNA capsule 1020 which may be punched out of the well directly above or forced through the opening 1140 by the portion 1015 of the plunger 1010.

A first linear actuator 1145 is coupled to a bottom valve layer 1150 having an exit opening 1152. The first linear actuator 1145 may be used to provide a valve function for the chamber 1120. As shown, the valve is open, allowing DNA solution to exit the rehydration unit 1100 via a fluidic tube 1155. The first linear actuator 1145 may controllably move the bottom valve layer 1150 laterally to close the valve by making sure the exit opening 1152 is not overlapping with chamber 1120. Again, mating polished surfaces of the layers provides for a fluidic seal.

A second linear actuator 1160 is coupled to a chamber layer 1165 disposed between the filter layer 1115 and the bottom valve layer 1150. The adjacent surfaces of each layer are also hardened, flat, and polished to provide a liquid seal. Second linear actuator 1160 may be used to agitate the chamber 1120 in a manner conducive to facilitating a rehydration of the DNA. Note that the use of hardened, flat, polished surfaces provides for low-friction lateral movement and also vertical retentive force, as it usually requires significant vertical force to separate polished surfaces in contact with each other. Thus, the various layers of the rehydration unit 1100 stay coupled absent an external vertical force applied to them. In some embodiment, the layers may be disposed or otherwise supported in a container that provides some vertical force, as well as a horizontal force to at least one non-moving layer such that the actuators only move one layer at a time in a controlled manner, as controlled by the electronics module, such as electronics 310, or an external electronics module. The container may provide support for the actuators, which may be used to support the layers and lock the layers in position when not moving their respective layers.

Figure 5:
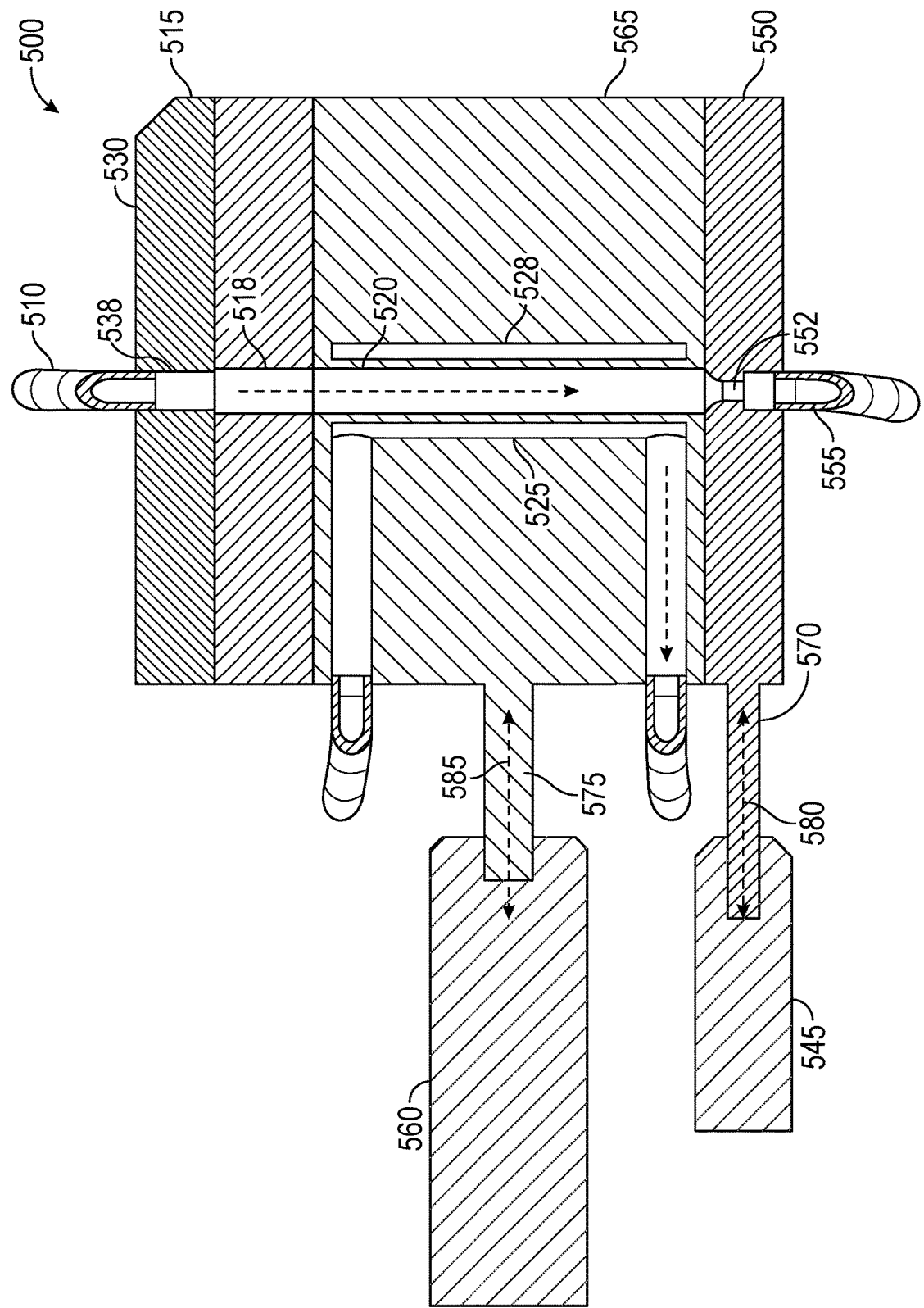
FIG. 5 is a block cross section of a flexible chemistry reaction chamber module unit for amplifying data-encoded DNA according to an example embodiment.

Next, the retrieved and rehydrated DNA may be filtered and then subjected to PCR using the same process and equipment as illustrated at 500 in FIG. 5 but coupled to receive DNA solution from rehydration unit 1100 via suitable fluidics, such as one or more tubes and valves. Additional sequencing preparation steps can be performed in the flexible chemistry reaction chamber 1120 or a series of such chambers if necessary.

FIG. 11B is a semi-transparent perspective view of a combined reaction chamber and rehydration module 1162 with like components labeled consistently with unit 1100. A filter layer 1170 may be similar to filter layer 515 in FIG. 5 and is positioned between the top valve layer 1130 and the chamber layer 1165. A passage 1112 is disposed through the filter layer 1170. An additional tube 1175 is provided laterally spaced from tube 1110. The third linear actuator 1135 is coupled to move both the top valve layer 1130 and the filter layer 1170 to provide either a filtered passage to the reaction chamber 1120 or a clear passage or path to the reaction chamber 1120. Moving the combined tube 1110 and passage 1112 to align with the reaction chamber 1120 provides a clear passage for a capsule 1020 of DNA to the reaction chamber 1120 for rehydration and/or de-encapsulation. In this mode, the module 1162 acts in a manner similar to the rehydration unit 1100. Moving the tube 1175 and filter layer 1170 to align with the reaction chamber 1120 provides a filtered path for receiving DNA from other units and performing PCR.

Bottom valve layer 1150, actuated via first linear actuator 1145, may be formed of, or include, filter material that may be similar to the filter material in filter layer 1170. In addition to tube 1155, which has a clear passage or path through the layer 1150 as indicated at passage 1156, layer 1150 may also include a further tube 1180 laterally spaced from the tube 1155 for first filtering the solution and then exiting solution when aligned with the reaction chamber 1120 via the first linear actuator 1145. Module 1162 may also include the heating elements and other thermal loops to facilitate DNA processing.

In one embodiment, once the DNA is rehydrated or otherwise ready for further processing in the reaction chamber 1120, other reagents may be added through tube 1110 and the valves may be controlled to close the reaction chamber 1120. Various cycles of heat and/or vibration may then be applied via the actuators and heating mechanisms depending on the reaction desired. Other reagents may be added with additional cycles performed as many times as called for by the selected reaction. The resulting solution may then be output via a filter.

Filtering of solutions being processed in the reaction chamber 1120 may be accomplished by first passing the solutions through the filter material such that DNA is captured by the filter. The fluid from the solution from the chamber 1120 flows through the chamber 1120 and out to waste or recycling containers. A second fluid may be introduced into the chamber 1120 and used to elute the DNA from the filter. The second fluid may have a volume that is much less than the volume of fluids used for processing the DNA. During elution, the chamber 1120 may be closed such that the DNA remains in the chamber 1120. The eluted DNA may then be provided to other units or modules for further processing, such as sequencing or storage, via tube 1155.

In one embodiment, module 1162 may also prepare the rehydrated DNA for sequencing. One or more processing steps, such as ligation, may be used to prepare the DNA for sequencing for some sequencing methods. Module 1162 may include fluidics coupled between an output to an input of the reaction chamber 1120 to achieve several ligation or other preparation cycles. The types of cycles may be dependent on subsequent sequencing methods utilized. In further embodiments, multiple modules 1162 may be serially fluidically coupled to perform such ligation cycles.

The actuators may be controlled to isolate the processing chamber 1120 from all inputs and outputs for agitating or otherwise moving the chamber 1120 to mix fluids and DNA. Such isolation may be obtained by any combination of actuator positioning in various embodiments. In further embodiments, actuators need not be positioned on a same side of the module 1162 and could be positioned on opposite sides or at various angles from each other while also repositioning the inputs and outputs accordingly to account for the motions of the layers in different directions.

Figure 12:
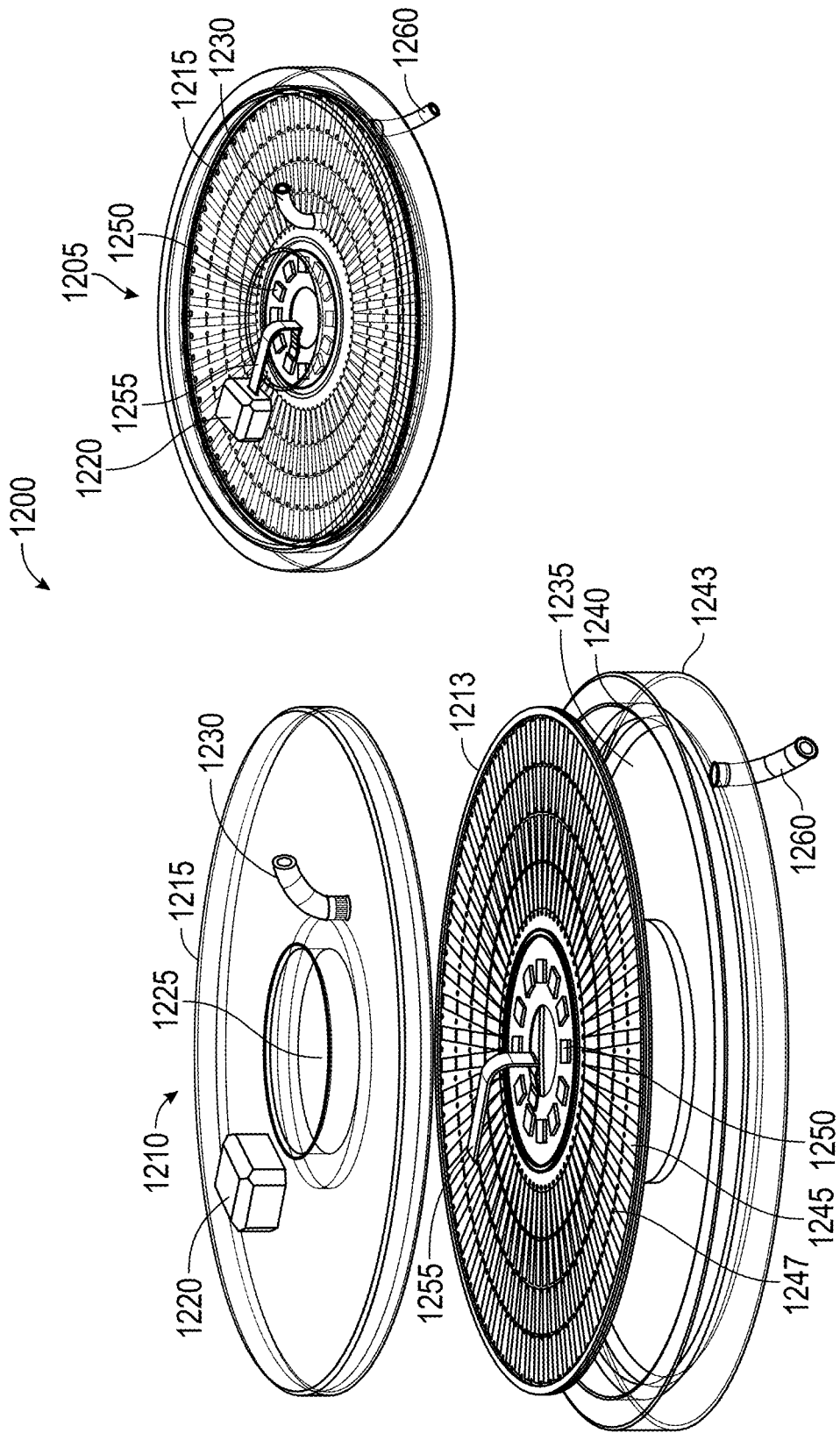
FIG. 12 is a block perspective and exploded block perspective view of a sequencing module according to an example embodiment.

Finally, the DNA is moved into a sequencing module 1200 shown in a partially assembled perspective view of wafer 1205 and exploded perspective view of the sequencing module at 1210 in FIG. 12. The sequencing module 1200 may be the same as or similar to synthesis module or unit 400 shown in FIG. 4. In one embodiment, one or more wafers 1213 (one shown) are clamped in a stack between a top layer 1215 having an electronics module 1220, an opening 1225, and a fluid inlet tube 1230. The wafer or wafers 1213 are encapsulated within a chamber 1235 formed by an open cylindrical structure 1240 that is bolted or clamped with the top layer 1215 and supported within an outer shell 1243. A top portion of the outer shell 1243 is omitted for illustration purposes. Structure 1240 is supported by a controllable rotating support, not shown.

The wafer 1213 may be the same as wafer 300 in FIG. 3, and may also include multiple radially arranged reticles 1245, electronics 1250, and a flex circuit 1255 that couples to electronics module 1220. Note that electronics module 1220 may serve as a connector between electronics 1250 and an external controller. Sequencing module 1200 may also include a fluid exit opening and tube 1260 to facilitate removal of fluids and DNA solution from the sequencing module 1200. In one embodiment sequencing module 1200 may rotate to aid in removing liquid during various steps of the sequencing process.

The reticles 1245 may be used to read the DNA sequences. The output is a digital representation of the information encoded in the DNA sequences. DNA may be attracted to the reticles 1245 by a difference in voltage. In one embodiment, a voltage may be applied to draw the DNA through nanopores in the reticles 1245. The nanopores may then be read, with the data provided to the file system and controller 181. Reading mechanisms 1247 may be nanopore-based, optical, electronic, or other. In further embodiments, other sequencing methods may be used.

Figure 13:
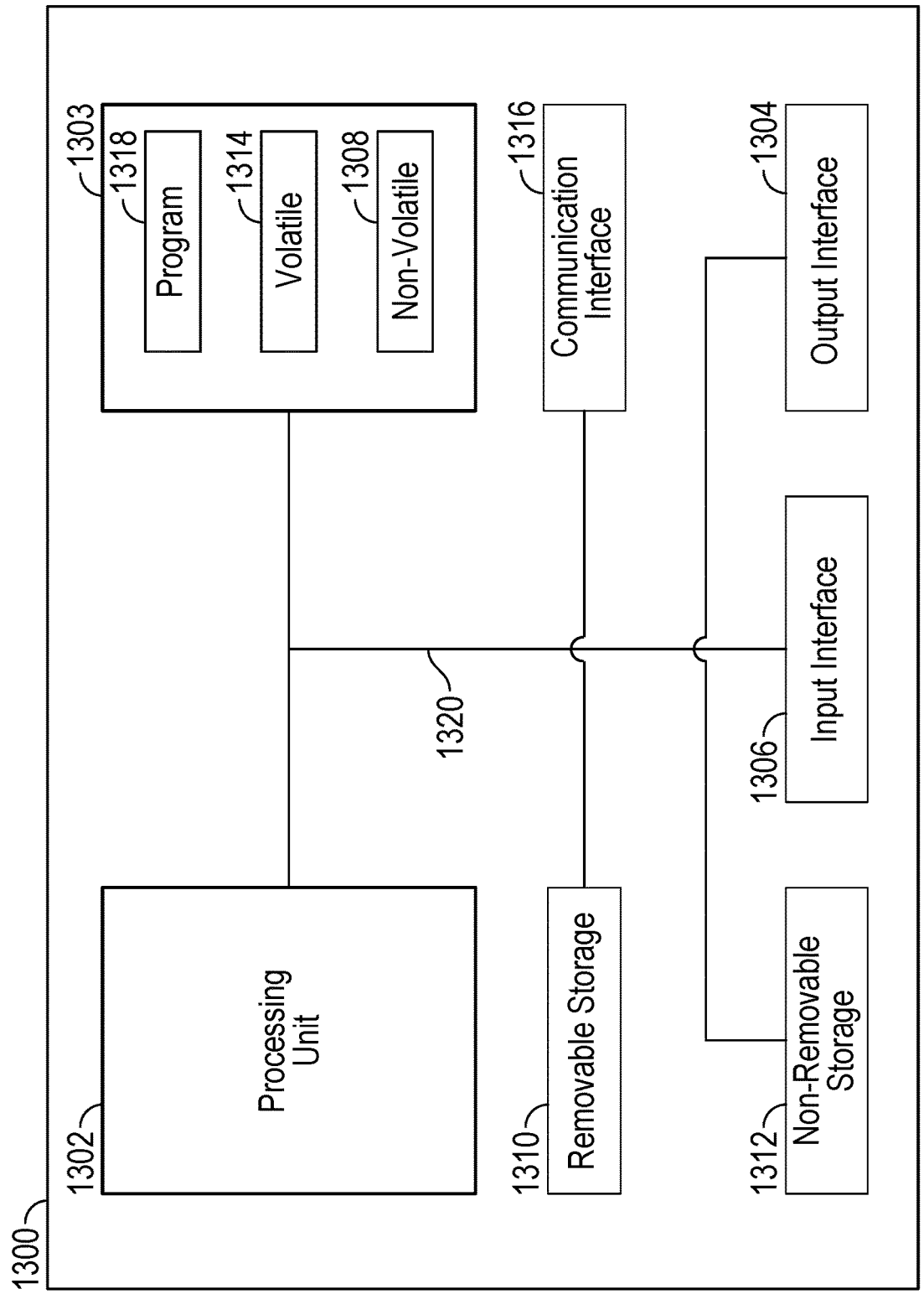
FIG. 13 is a block schematic diagram of a computer system to implement one or more methods and control devices according to example embodiments.

FIG. 13 is a block schematic diagram of a computer system 1300 to implement a controller for controlling components, fluidics, and robots for synthesizing, storing, and retrieving data-encoded DNA and for performing methods and algorithms according to example embodiments. All components need not be used in various embodiments.

One example computing device in the form of a computer system 1300 may include a processing unit 1302, memory 1303, removable storage 1310, and non-removable storage 1312. Although the example computing device is illustrated and described as computer system 1300, the computing device may be in different forms in different embodiments. For example, the computing device may instead be a smartphone, a tablet, smartwatch, smart storage device (SSD), or other computing device including the same or similar elements as illustrated and described with regard to FIG. 13.

Devices, such as smartphones, tablets, and smartwatches, are generally collectively referred to as mobile devices or user equipment. Still further, system 1300 may be implemented as a cloud-based service or in one or more electronics modules separate from or integrated with the various components for processing DNA described herein.

Although the various data storage elements are illustrated as part of the computer system 1300, the storage may also or alternatively include cloud-based storage accessible via a network, such as the Internet or server-based storage. Note also that an SSD may include a processor on which the parser may be run, allowing transfer of parsed, filtered data through I/O channels between the SSD and main memory.

Memory 1303 may include volatile memory 1314 and non-volatile memory 1308. Computer system 1300 may include—or have access to a computing environment that includes—a variety of computer-readable media, such as volatile memory 1314 and non-volatile memory 1308, removable storage 1310 and non-removable storage 1312. Computer storage includes random access memory (RAM), read-only memory (ROM), erasable programmable read-only memory (EPROM) or electrically erasable programmable read-only memory (EEPROM), flash memory or other memory technologies, compact disc read-only memory (CD ROM), Digital Versatile Disks (DVD) or other optical disk storage, magnetic cassettes, magnetic tape, magnetic disk storage or other magnetic storage devices, or any other medium capable of storing computer-readable instructions.

Computer system 1300 may include or have access to a computing environment that includes input interface 1306, output interface 1304, and a communication interface 1316. Output interface 1304 may include a display device, such as a touchscreen, that also may serve as an input device. The input interface 1306 may include one or more of a touchscreen, touchpad, mouse, keyboard, camera, one or more device-specific buttons, one or more sensors integrated within or coupled via wired or wireless data connections to the computer, and other input devices. The computer may operate in a networked environment using a communication connection to connect to one or more remote computers, such as database servers. The remote computer may include a personal computer (PC), server, router, network PC, a peer device or other common data flow network switch, or the like. The communication connection may include a Local Area Network (LAN), a Wide Area Network (WAN), cellular, Wi-Fi, Bluetooth, or other networks. According to one embodiment, the various components of computer system 1300 are connected with a system bus 1320.

Computer-readable instructions stored on a computer-readable medium are executable by the processing unit 1302 of the computer system 1300, such as a program 1318. The program 1318 in some embodiments comprises software to control the various fluidics, pressure module, flexible chemistry reaction chamber modules, synthesizing units, sequencing units, robotics, actuators, and other components used in processing DNA for storage and retrieval. A hard drive, CD-ROM, and RAM are some examples of articles including a non-transitory computer-readable medium such as a storage device. The terms "computer-readable medium" and "storage device" do not include carrier waves to the extent carrier waves are deemed transitory. Storage can also include networked storage, such as a storage area network (SAN). Computer program 1318 may be used to cause processing unit 1302 to perform one or more methods or algorithms described herein.

Figure 14:
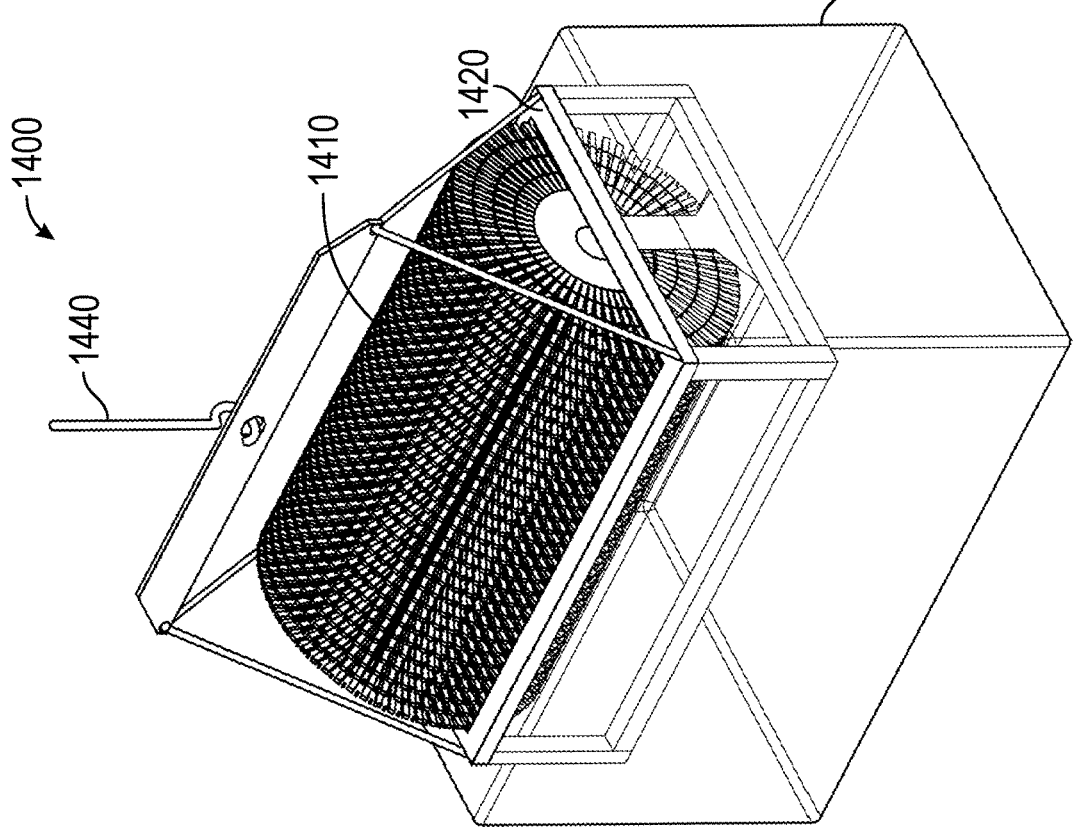
FIG. 14 is a perspective view of a system for processing a plurality of wafers held in a wafer boat according to an example embodiment.

FIG. 14 is a perspective view of a system 1400 for processing a plurality of wafers 1410 held in a wafer boat 1420. The boat 1420 may include features to support the wafers 1410 in a vertical orientation with spacing between the wafers 1410 to allow exposure to one or more liquids in one or more dipping bath containers 1430 via a cable 1440 coupled to the boat 1420. A wafer boat used for holding semiconductor wafers in common semiconductor processing processes may be used in one embodiment. System 1400 facilitates processing of wafers to synthesize DNA utilizing available semiconductor type trays and bath containers filled with reagents and other fluids used in common DNA processing methods.

Figure 15:
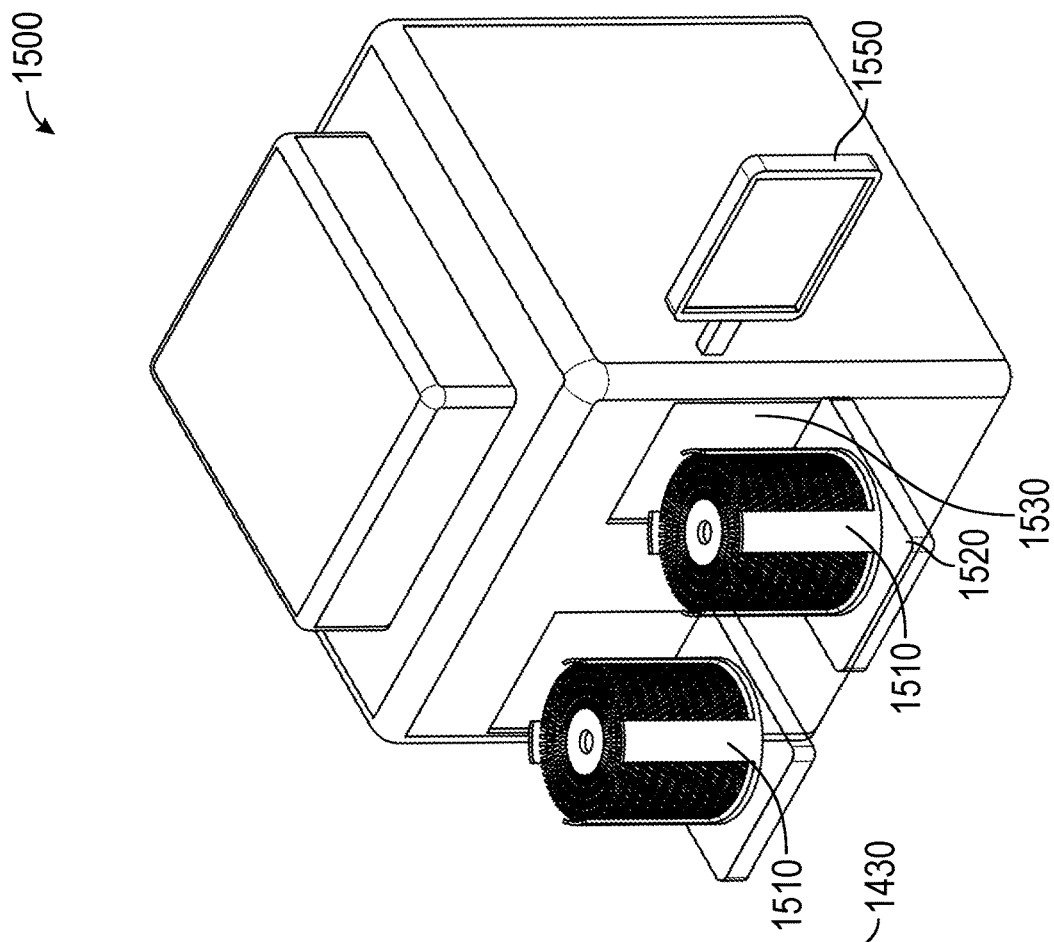
FIG. 15 is a perspective view of a device for processing one or more stacks of wafers according to an example embodiment.

FIG. 15 is a perspective view of a device 1500 for processing one or more stacks of wafers 1510 supported by one or more trays 1520. The trays 1520 may be moved into a chamber 1530 used for processing the wafers 1510. Device 1500 may be used for different processing steps, such as physical or chemical vapor deposition, chemical-mechanical planarization, lithography, annealing, and other processes that are performed by different semiconductor processing devices. One or more of different types of devices represented by device 1500 may be used in the processing of DNA on the wafers 1510, such as steppers for patterning, deposition machines, and others. An input/output device such as touchscreen 1550 may be used to control device 1500. Device 1500 may also be controlled via file system and controller 181 in further embodiments.

EXAMPLES

In example 1, a system includes a synthesizer unit having a fluid input to receive fluids and a communication input to receive commands to synthesize data-encoded DNA sequences and cleave the DNA. A first flexible chemistry reaction chamber module may be fluidically coupled to the synthesizer unit to receive the data encoded DNA sequences and amplify the sequences. A deposition unit may be fluidically coupled to the first flexible chemistry reaction chamber module to receive the amplified DNA sequences and encapsulate the amplified DNA sequences into one or more wells in a storage plate for storage and retrieval to and from a plate storage unit.

Example 2 includes the system of example 1 wherein the encapsulated DNA sequences are dried, and further comprising a rehydration and de-encapsulation unit coupled to receive the dried encapsulated DNA from a well in the storage plate and rehydrate the DNA.

Example 3 includes the system of any of examples 1-2 and further comprising a second flexible chemistry reaction chamber module coupled to receive rehydrated DNA from the rehydration and encapsulation unit and amplify DNA sequences.

Example 4 includes the system of example 3 and further comprises a sequencing unit coupled to receive amplified DNA sequences from the second flexible chemistry reaction chamber module.

Example 5 includes the system of example 4 wherein the sequencing unit sequences the amplified DNA sequences, reads the sequences, and provides a digital output representative of the sequences.

Example 6 includes the system of example 5 and further comprises a controller coupled to control the rehydration and de-encapsulation unit, second flexible chemistry reaction chamber module, sequencing unit, and fluidics for transferring DNA sequences therebetween.

Example 7 includes the system of any of examples 1-6 wherein the sequencing unit is coupled to provide the controller the digital output, and wherein the controller is configured to decode the digital output into the data encoded into the DNA sequences.

Example 8 includes the system of any of examples 1-7 and further comprises a storage unit configured to retrievably hold multiple storage plates.

Example 9 includes the system of any of examples 1-8 and further comprises a controller coupled to control the synthesizer unit, flexible chemistry reaction chamber module, and deposition unit and fluidics for transferring DNA sequences therebetween.

In example 10, a method includes synthesizing data-encoded DNA sequences and cleaving the DNA sequences via a synthesizer unit having a fluid input to receive fluids and a communication input to receive commands to synthesize data-encoded sequences and cleave the DNA, amplifying the DNA sequences via a first flexible chemistry reaction chamber module fluidically coupled to the synthesizer unit, and receiving the amplified DNA sequences and encapsulating the amplified DNA sequences via a deposition unit fluidically coupled to the first flexible chemistry reaction chamber module into one or more wells in a storage plate for storage and retrieval to and from a plate storage unit.

Example 11 includes the method of example 10 wherein the encapsulated DNA comprises dried DNA, and further including receiving the encapsulated DNA from a well in the storage plate at a rehydration and de-encapsulation unit and rehydrating and recovering the encapsulated DNA.

Example 12 includes the method of example 11 and further includes amplifying the rehydrated DNA at a second flexible chemistry reaction chamber module coupled to receive rehydrated DNA from the rehydration and encapsulation unit and preparing the amplified DNA for sequencing.

Example 13 includes the method of example 12 and further includes receiving the amplified and prepared DNA from the second flexible chemistry reaction chamber module at a sequencing unit fluidically coupled to the second flexible chemistry reaction chamber module and providing a digital output representative of the sequences.

Example 14 includes the method of example 13 and further includes controlling the rehydration and de-encapsulation unit, second flexible chemistry reaction chamber module, sequencing unit, and fluidics for transferring DNA sequences therebetween via a computer implemented controller.

Example 15 includes the method of example 14 wherein the controller is configured to receive the digital output and decode the binary output into the data encoded into the DNA sequences.

Example 16 includes the method of any of examples 10-15 and further comprises controlling, via a computer-implemented controller, the synthesizer unit, flexible chemistry reaction chamber module, deposition unit, and fluidics for transferring DNA sequences therebetween.

In example 17, a machine-readable storage device has instructions for execution by a processor of the machine to perform operations. The operations include controlling synthesizing data-encoded DNA sequences and cleaving the DNA sequences via a synthesizer unit having a fluid input to receive fluids and a communication input to receive commands to synthesize data-encoded sequences and cleave the DNA, controlling amplifying the DNA sequences via a first flexible chemistry reaction chamber module fluidically coupled to the synthesizer unit, and controlling receiving of the amplified DNA sequences and encapsulated the amplified DNA sequences via a deposition unit fluidically coupled to the first flexible chemistry reaction chamber module into one or more wells in a storage plate for storage and retrieval to and from a plate storage unit.

Example 18 includes the machine-readable storage device of example 17 wherein the encapsulated DNA sequences comprise dried DNA sequences, and further including controlling receiving the encapsulated DNA from a well in the storage plate at a rehydration and de-encapsulation unit and controlling rehydrating and recovering the encapsulated DNA.

Example 19 includes the machine-readable storage device of example 18 and further includes controlling amplifying the rehydrated DNA and preparing the amplified DNA for sequencing at a second flexible chemistry reaction chamber module coupled to receive rehydrated DNA from the rehydration and encapsulation unit, controlling receiving the amplified DNA from the second flexible chemistry reaction chamber module at a sequencing unit fluidically coupled to the second flexible chemistry reaction chamber module, and controlling providing a digital output representative of the sequences.

Example 20 includes the machine-readable storage device of any of examples 17-19 and further comprises controlling the rehydration and de-encapsulation unit, second flexible chemistry reaction chamber module, sequencing unit, and fluidics for transferring DNA sequences therebetween via a computer-implemented controller.

SECOND SET OF EXAMPLES

In example 1, a system processes DNA sequences. The system includes a synthesis unit having a synthesis chamber with a wafer-shaped substrate having multiple reticles for synthesizing DNA sequences, the synthesis unit having an input for receiving DNA sequences and processing fluids, and an output for eluting synthesized DNA in a DNA solution, a flexible chemistry reaction chamber module for processing the DNA sequences, the flexible chemistry reaction chamber module having an input and an output, a deposition DNA unit having an input and an output, multiple plates having wells for holding DNA, a storage library having slots for holding plates, a rehydration unit having multiple inputs and an output to rehydrate DNA, a second flexible chemistry reaction chamber module for processing rehydrated DNA sequences, a sequencer unit having a sequencing chamber with a wafer-shaped substrate having multiple reticles for sequencing DNA sequences, the sequencer unit having an input for receiving processed DNA sequences and a digital signal output, a fluidic network coupled to the units for transferring DNA sequences between the units and providing processing fluids to the units, and a robot coupled to transfer plates between units.

Example 2 includes the system of example 1 and further includes a controller coupled to control the units, fluidics, and robot.

Example 3 includes the system of any of examples 1-2 and further comprises a pressure control unit coupled to vary pressure in one or more of the synthesis unit, flexible chemistry reaction chamber module, rehydration unit, second flexible chemistry reaction chamber module, and sequencer unit.

Example 4 includes the system of example 3 wherein the pressure control unit decreases pressure to fill chambers and increases pressure to evacuate fluids from the chambers.

Example 5 includes the system of example 3 wherein the fluidic network is further coupled to the units and modules for transferring DNA between the units and modules.

Example 6 includes the system of any of examples 1-5 wherein the robot is configured to position the plates for deposition of the DNA in the wells, insert and retrieve the plates in selected slots of the storage library, and position plates for inserting DNA from the wells into the dehydration unit.

Example 7 includes the system of any of examples 1-6 wherein the units and modules are supported in rack units.

Example 8 includes the system of any of examples 1-7 wherein the second flexible chemistry reaction chamber comprises recirculating fluidics for preparing the amplified DNA for sequencing.

Example 9 includes the system of example 8 wherein the recirculating fluidics facilitate multiple preparation cycles to prepare the amplified DNA for sequencing.

Example 10 includes the system of any of examples 1-9 wherein the deposition DNA unit is operable to encapsulate the DNA by adding other chemicals to the DNA, depositing the DNA and chemicals in the wells, and drying the DNA.

Example 11 includes the system of example 10 wherein the deposition DNA unit is further operable to seal the wells holding the DNA to encapsulate the DNA.

Example 12 includes the system of any of examples 10-11 wherein the deposition DNA unit is further operable to dry the DNA and chemicals in the wells.

Example 13 includes the system of any of examples 1-12 wherein the robot is coupled to transfer the plates between the deposition DNA unit, storage library slots, and rehydration unit.

In example 14, a computer-implemented method for processing DNA sequences includes controlling a synthesis unit having a synthesis chamber with a wafer-shaped substrate having multiple reticles for synthesizing DNA sequences, to receive DNA sequences and processing fluids, to synthesize the DNA sequences and output the synthesized DNA in a DNA solution, controlling a flexible chemistry reaction chamber module to receive the synthesized DNA and reagents and process the DNA sequences, controlling a deposition DNA unit to deposit the DNA sequences onto wells of a plate, controlling a robot to place the plates into slots of a storage library and transferring plates from the storage library to a rehydration unit, controlling the rehydration unit to rehydrate DNA, controlling a second flexible chemistry reaction chamber module to prepare the rehydrated DNA sequences for sequencing, and controlling a sequencer unit having a sequencing chamber with a wafer-shaped substrate having multiple reticles for sequencing DNA sequences to receive the prepared DNA sequences and provide a digital signal output.

Example 15 includes the method of example 14 wherein the deposition DNA unit is operable to encapsulate the DNA by adding other chemicals to the DNA, drying the DNA, and depositing the DNA and chemicals in the wells.

Example 16 includes the method of example 15 wherein the deposition DNA unit is further operable to seal the wells holding the DNA to encapsulate the DNA.

Example 17 includes the method of any of examples 15-16 wherein the deposition DNA unit is further operable to dry the DNA and chemicals in the wells.

Example 18 includes the method of any of examples 14-17 and further comprises controlling a fluidic network coupled to the units to transfer DNA sequences between the units and provide processing fluids to the units.

Example 19 includes the method of any of examples 14-18 and further comprises controlling a pressure control unit coupled to vary pressure in one or more of the synthesis unit, flexible chemistry reaction chamber module, rehydration unit, second flexible chemistry reaction chamber module, and sequencer unit.

Example 20 includes the method of example 19 wherein the pressure control unit is controlled to decrease pressure to fill chambers of the modules and units and increase pressure to evacuate fluids from the chambers.

Example 21 includes the method of any of examples 19-20 wherein the fluidic network is further controlled to transfer DNA between the units and modules.

Example 22 includes the method of any of examples 14-21 wherein the robot is controlled to position the plates for deposition of the DNA in the wells, insert and retrieve the plates in selected slots of the storage library, and position plates for inserting DNA from the wells into the dehydration unit.

Example 23 includes the method of any of examples 14-22 wherein the second flexible chemistry reaction chamber is controlled to recirculate fluidics for preparing the amplified DNA for sequencing.

In example 24, a system for processing DNA sequences includes a synthesis unit having inputs for receiving signals representing DNA sequences and processing fluids, and an output for eluting synthesized DNA in a DNA solution, a first flexible chemistry reaction chamber module for amplifying the DNA sequences, the first flexible chemistry reaction chamber module having an input and an output a deposition DNA unit having an input and an output multiple plates having wells for holding DNA, a storage library having slots for holding plates, rehydration unit having multiple inputs and an output to rehydrate DNA, a second flexible chemistry reaction chamber module for processing rehydrated DNA sequences, a sequencer unit having an input for receiving processed DNA sequences and a digital signal output, a fluidic network coupled to the units for transferring DNA sequences between the units and providing processing fluids to the units, and a robot coupled to transfer plates between the units.

Example 25 includes the system of example 24 and further comprises a controller coupled to control the units, fluidics, and robot.

Example 26 includes the system of any of examples 24-25 and further comprises a pressure control unit coupled to vary pressure in one or more of the synthesis unit, first flexible chemistry reaction chamber module, rehydration unit, second flexible chemistry reaction chamber module, and sequencer unit, wherein the pressure control unit decreases pressure to fill chambers and increases pressure to evacuate fluids from the chambers, and wherein the robot is configured to position the plates for deposition of the DNA in the wells, insert and retrieve the plates in selected slots of the storage library, and position plates for inserting DNA from the wells into the dehydration unit.

Example 27 includes the system of any of examples 24-26 wherein the second flexible chemistry reaction chamber comprises recirculating fluidics for preparing the amplified DNA for sequencing, wherein recirculating fluidics facilitates multiple ligation cycles to prepare the amplified DNA for sequencing.

Example 28 includes the system of any of examples 24-26 wherein the first flexible chemistry reaction chamber comprises recirculating fluidics for preparing the amplified DNA for sequencing, wherein recirculating fluidics facilitates multiple ligation cycles to prepare the amplified DNA for sequencing.

THIRD SET OF EXAMPLES

In example 1, a device includes a container forming a cavity, a fluidic input coupled through the container to the cavity, a fluidic output coupled through the container, and a stack of wafers vertically coupled to rotate about an axis supported within the cavity, wherein the wafers include one or more reticles to process DNA sequences.

Example 2 includes the device of example 1 wherein the device includes a communication interface.

Example 3 includes the device of any of examples 1-2 wherein the communication interface is operable to receive a digital representation identifying DNA sequences to synthesize.

Example 4 includes the device of any of examples 1-3 wherein the communication interface is operable to transmit a digital representation of data obtained from sequenced DNA.

Example 5 includes the device of any of examples 1-4 wherein the reticles are formed in a pattern extending radially outward on each wafer.

Example 6 includes the device of example 5 wherein the reticles are formed in concentric circles about a center of each wafer.

Example 7 includes the device of any of examples 5-6 wherein the reticles are separated by one or more fiducials disposed between the reticles.

Example 8 includes the device of any of examples 1-7 and further comprises multiple gaskets disposed between the wafers about an inner opening of the wafers.

Example 9 includes the device of any of examples 1-8 wherein the inner opening in combination with the wafers form an internal dry column.

Example 10 includes the device of any of examples 1-9 wherein the fluidic output is positioned proximate a periphery of the cavity.

Example 11 includes the device of any of examples 1-10 wherein the fluidic input is coupled to a pressure source to facilitate evacuation of fluids from the cavity by increasing pressure in the cavity.

Example 12 includes the device of any of examples 1-11 wherein the fluidic output is coupled to a pressure source to facilitate filling of the cavity with fluids by decreasing pressure in the cavity.

Example 13 includes the device of any of examples 1-12 and further includes multiple valves coupled to control the flow of fluids in the fluidic input and fluidic output.

Example 14 includes the device of any of examples 1-13 and further comprises a motor coupled to controllably rotate the stack of wafers to remove fluid from the wafers for elution via the fluidic output.

Example 15 includes the device of example 14 wherein the motor rotates the stack of wafers up to approximately 1000 revolutions per minute.

In example 16, a device includes a container forming a cavity, a fluidic input coupled through the container to the cavity, a fluidic output coupled through the container to elute fluids from the cavity, a communication connection, and a stack of wafers vertically coupled to rotate about an axis supported within the cavity, wherein the wafers include one or more reticles to process DNA sequences and wherein the communication connection receives data identifying DNA sequences to synthesize and transmits data representative of sequenced DNA.

In example 17 a method includes receiving fluids in a cavity of a container, the fluids being received via a fluidic input coupled through the container to the cavity, eluting fluids via a fluidic output coupled through the container to the cavity, and rotating a stack of wafers vertically coupled about an axis supported within the cavity, wherein the wafers include one or more reticles to process DNA sequences.

Example 18 includes the method of example 17 and further comprises receiving digital data defining DNA that encodes information to be stored, or transmitting digital data representative of sequenced information encoded DNA.

Example 19 includes the method of any of examples 17-18 and further comprises increasing pressure in the cavity while rotating the stack of wafers to elute fluid through the output port positioned proximate a periphery of the wafers.

Example 20 includes the method of any of examples 17-19 and further includes controlling fluidic valves to selectively provide DNA processing fluids to the cavity via the fluidic input and selectively elute DNA from the cavity via the fluidic output.

FOURTH SET OF EXAMPLES

In example 1, a device includes a plurality of round wafers coaxially mounted in a stack and a plurality of DNA processing reticles disposed about the wafers to process DNA sequences, wherein the wafers are rotatably coupled about a central axis of the wafers to remove DNA processing fluids from the wafers in response to rotation of the wafers.

Example 2 includes the device of example 1 wherein the wafers have a central opening, the device further comprising a gasket disposed between adjacent wafers about the central opening.

Example 3 includes the device of example 2 wherein the gasket is circular in shape and provides a seal between the adjacent wafers.

Example 4 includes the device of any of examples 2-3 wherein the reticles are arranged in a pattern extending radially from the gasket.

Example 5 includes the device of example 4 wherein the reticles are processing sites to hold fluid during DNA processing.

Example 6 includes the device of example 4 wherein the reticles are a same size and are arranged in concentric circles of reticles about the central opening.

Example 7 includes the device of any of examples 2-6 and further comprises a plurality of standoff wafer pitch fiducials formed between the reticles.

Example 8 includes the device of any of examples 2-7 and further comprises electronic modules supported on the wafers between the inner opening and gasket and a flex circuit coupled to the electronic modules.

Example 9 includes the device of any of examples 1-8 wherein the reticles further comprise nanopores through which DNA is drawn in response to an applied voltage.

Example 10 includes the device of any of examples 1-9 wherein the reticles are functionalized.

Example 11 includes the device of any of examples 1-10 wherein the wafers are formed of silicon.

Example 12 includes the device of any of examples 1-8 wherein the reticles are configured to manipulate the DNA.

In example 13, a device includes a wafer, a plurality of DNA sequencing reticles disposed about the wafer to process DNA sequences, wherein the wafer is rotatable about a central axis of the wafer to remove DNA processing fluids from the wafers in response to rotation of the wafer.

Example 14 includes the device of example 13 wherein the wafer has a central opening.

Example 15 includes the device of example 14 wherein the reticles are arranged in a pattern extending radially from the central opening.

Example 16 includes the device of example 15 wherein the reticles are processing sites to hold fluid during DNA processing.

Example 17 includes the device of example 16 wherein the reticles are a same size and are arranged in concentric circles of reticles about the central opening.

Example 18 includes the device of any of examples 14-17 and further comprises a plurality of standoff wafer pitch fiducials formed between the reticles.

Example 19 includes the device of any of examples 12-18 and further includes electronic modules supported on the wafers between the inner opening and reticles and a flex circuit coupled to the electronic modules.

Example 20 includes the device of any of examples 14-19 wherein the reticles are functionalized.

In example 21, a method includes exposing a plurality of round wafers coaxially mounted in a stack to a DNA processing fluid to process DNA sequences on a plurality of DNA processing reticles disposed about the wafers and rotating the stack of wafers about a central axis of the wafers to remove the DNA processing fluid from the wafers.

FIFTH SET OF EXAMPLES

In example 1, a DNA processing module includes a DNA processing chamber layer having a DNA processing chamber disposed therein, a top layer having a first input alignable with the DNA processing chamber, a bottom valve layer having a first output alignable with the DNA processing chamber, a first actuator coupled to move the DNA processing chamber layer laterally between the top layer and the bottom valve layer, and a second actuator coupled to move the bottom valve layer to selectively seal and elute DNA from the DNA processing chamber.

Example 2 includes the DNA processing module of example 1 and further comprises a filter layer coupled to the top layer and disposed between the top layer and the chamber layer.

Example 3 includes the DNA processing module of example 2 and further comprises a second input laterally spaced from the first input in the top layer, wherein the filter layer comprises a passage aligned with the first input and a filter material between the second input and the processing chamber.

Example 4 includes the DNA processing module of example 3 and further comprises a third actuator coupled to the top layer and filter layer to selectably align the first and second inputs with the processing chamber.

Example 5 includes the DNA processing module of any of examples 1-4 wherein adjacent layers comprise polished hardened surfaces to form laterally movable seals between the layers.

Example 6 includes the DNA processing module of any of examples 1-5 and further comprising a thermal fluid circulation loop thermally coupled to the processing chamber.

Example 7 includes the DNA processing module of any of examples 1-6 and further comprises a second, filtered output in the bottom valve layer, wherein the second actuator moves the bottom valve layer to provide a filtered or unfiltered output.

Example 8 includes the DNA processing module of any of examples 1-7 and further comprises a heating element thermally coupled to the processing chamber in the chamber layer.

Example 9 includes the DNA processing module of any of examples 1-8 wherein the first actuator is operable to agitate the processing chamber.

Example 10 includes the DNA processing module of any of examples 1-9 wherein at least one of the outputs is fluidically coupled to at least one of the inputs to prepare DNA for sequencing.

In example 11, a DNA processing module includes a DNA processing chamber layer having a DNA processing chamber disposed therein, a top layer having a first input and a second input alignable with the DNA processing chamber, a bottom valve layer having a first output and a second output alignable with the DNA processing chamber, a first actuator coupled to move the DNA processing chamber layer laterally between the top layer and the bottom valve layer, a second actuator coupled to move the bottom valve layer to selectively seal and elute DNA from the DNA processing chamber, and a third actuator coupled to laterally move the top layer.

Example 12 includes the DNA processing module of example 11 and further comprises a filter layer coupled to the top layer and disposed between the top layer and the chamber layer.

Example 13 includes the DNA processing module of example 12 wherein the second input is laterally spaced from the first input in the top layer and wherein the filter layer comprises a passage aligned with the first input and a filter material between the second input and the processing chamber.

Example 14 includes the DNA processing module of example 13 wherein the third actuator is coupled to the top layer and filter layer to selectably align the first and second inputs with the processing chamber.

Example 15 includes the DNA processing module of any of examples 11-14 wherein adjacent layers comprise polished hardened surfaces to form laterally movable seals between the layers.

Example 16 includes the DNA processing module of any of examples 11-15 and further comprises a thermal fluid circulation loop thermally coupled to the processing chamber.

Example 17 includes the DNA processing module of any of examples 11-16 and further comprises a heating element thermally coupled to the processing chamber in the chamber layer.

In example 18, a method includes receiving fluid through a first input in a top layer of a DNA processing module, moving the received fluid into a processing chamber in a processing chamber layer adjacent to the top layer, isolating the processing chamber from the first input and a first output in a bottom valve layer adjacent to the processing chamber layer to process DNA with the fluid, and eluting fluid and DNA from the first output of the bottom valve layer.

Example 19 includes the method of example 18 wherein the adjacent layers comprise polished hardened surfaces to form laterally moveable seals, and wherein adjacent layers are moved by first and second actuators coupled to the processing chamber layer and bottom valve layers respectively.

Example 20 includes the method of any of examples 18-19 and further comprises laterally moving the top layer to selectively align the first input and a second, filtered input with the processing chamber via a third actuator.

In example 21, a method includes capturing DNA in a filter as a first fluid with DNA in a processing chamber of a DNA processing module passes through the filter, eluting DNA from the filter with a second fluid in the processing chamber, and removing the second fluid and DNA from the processing chamber.

Example 22 includes the method of example 21 wherein the second fluid volume is less than the first fluid volume.

In example 23, a method includes adding reagents through a first passage in a processing chamber of a DNA processing module, the processing chamber having DNA therein, closing the processing chamber, processing the DNA in the reagents, repeating the adding, closing, and processing elements a selected number of times, and removing the reagents and DNA from the processing chamber via a second passage.

SIXTH SET OF EXAMPLES

In example 1, a DNA storage device includes a plate having a depth, a length, and a width, an array of wells formed on the plate, wherein the wells are shaped to hold DNA sequences, and a storage library having a plurality of robotically addressable slots, the slots sized to accommodate the depth, length, and width of the plate.

Example 2 includes the DNA storage device of example 1 wherein the wells extend through the depth of the plate.

Example 3 includes the DNA storage device of example 2 and further comprising a first membrane on a first side of the plate to hold DNA within one or more wells.

Example 4 includes the DNA storage device of example 3 and further comprising a second membrane on a second side of the plate such that DNA is held within one or more wells between the first and second membranes.

Example 5 includes the DNA storage device of example 4 wherein the DNA sequences are in solution between the first and second membranes.

Example 6 includes the DNA storage device of example 4 wherein the DNA sequences are dehydrated.

Example 7 includes the DNA storage device of any of examples 1-6 wherein the plate includes a visual code on an end of the plate visible while the plate is in a slot of the storage library, the visual code uniquely identifying the plate.

Example 8 includes the DNA storage device of any of examples 1-7 and further comprises a transport protrusion coupled to a first end of the plate.

Example 9 includes the DNA storage device of example 8 and further comprises a pair of opposing retention protrusions coupled to a second end of the plate, the retention protrusions formed to releasably couple to a retention post when the plate is fully inserted into a slot.

Example 10 includes the DNA storage device of any of examples 1-9 wherein the storage library slots each have a physical location and corresponding logical address.

Example 11 includes the DNA storage device of any of examples 1-10 wherein the storage library comprises one or more flanges for attaching the storage library to an equipment rack.

In example 12, a DNA storage device includes a plate having a depth, a length, and a width, an array of wells formed on the plate, wherein the wells are shaped to hold DNA sequences, and a transport protrusion coupled to a first end of the plate for use by a robot to transport the plate to and from a storage library having a plurality of robotically addressable slots, the slots sized to accommodate the depth, length, and width of the plate.

Example 13 includes the DNA storage device of example 12 wherein the wells extend through the depth of the plate.

Example 14 includes the DNA storage device of example 13 and further comprises a first membrane on a first side of the plate to hold DNA within one or more wells.

Example 15 includes the DNA storage device of example 14 and further comprises a second membrane on a second side of the plate such that DNA is held within one or more wells between the first and second membranes.

Example 16 includes the DNA storage device of any of examples 12-15 wherein the plate includes a visual code on an end of the plate visible while the plate is in a slot of the storage library, the visual code uniquely identifying the plate.

Example 17 includes the DNA storage device of any of examples 12-16 and further comprises a pair of opposing retention protrusions coupled to a second end of the plate, the retention protrusions formed to releasably couple to a retention post when the plate is fully inserted into a slot.

Example 18 includes the DNA storage device of any of examples 12-17 wherein the storage library slots each have a physical location and corresponding logical address.

In example 19, a method includes depositing DNA encoded with selected data into one or more wells of a plate having a depth, a length, and a width, the wells formed in an array on the plate, wherein the wells are shaped to hold DNA sequences, and engaging a transport protrusion coupled to a first end of the plate by a robot to transport the plate to and from a storage library having a plurality of robotically addressable slots, the slots sized to accommodate the depth, length, and width of the plate.

Example 20 includes the method of example 19 wherein the wells extend through the depth of the plate.

Example 21 includes the method of example 20 and further includes forming a first membrane on a first side of the plate to hold DNA within one or more wells and forming a second membrane on a second side of the plate such that DNA is held within one or more wells between the first and second membranes.

Example 22 includes the method of any of examples 19-21 wherein the plate includes a visual code on an end of the plate visible while the plate is in a slot of the storage library, the visual code uniquely identifying the plate, the method including reading the visual code to verify that the plate is in a correct slot.

In example 21, a method of using the slide having an array of cavities includes providing metadata, or a pointer thereto, describing data stored in the form of encoded DNA in the cavities, wherein the slide includes a membrane for allowing removal of fluid while encapsulating the DNA in the cavities and optional drying of the DNA, wherein the slide is configured to be inserted in a storage container with other slides, and removable therefrom for pushing out encapsulated DNA from a selected cavity for de-encapsulation and reading.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A device comprising:
    a chamber configured to rotate about a central axis;
    a plurality of wafers stacked within the chamber and coaxially aligned with the central axis of the chamber;
    a rotating component of a motor device coupled to the plurality of wafers and configured to rotate the plurality of wafers;
    a plurality of DNA processing sites disposed on a surface of each wafer of the plurality of wafers to process DNA, wherein the device is configured to remove a reagent from the plurality of wafers by centrifugal force caused by rotation of the plurality of wafers about the central axis; and
    a controller communicatively coupled to the motor and programmed to cause the rotation of the plurality of wafers at a revolutions per minute (rpm) sufficient to create the centrifugal force to remove the reagent.

2. The device of claim 1, wherein the plurality of wafers is formed of silicon.

3. The device of claim 1, wherein each of the plurality of wafers has a central opening.

4. The device of claim 3, wherein the DNA processing sites on each wafer of the plurality of wafers are arranged in a pattern extending radially from the central opening toward a respective outer edge of each wafer.

5. The device of claim 3, wherein each of the DNA processing sites are a same size and are arranged in concentric circles of reticles about the central opening.

6. The device of claim 3, wherein the rotating component is configured to couple to the plurality of wafers through the central opening and rotate the plurality of wafers about the central axis.

7. The device of claim 1, wherein the rotating component of the motor device comprises a rotary servo drive.

8. The device of claim 1, wherein a wafer of the plurality of wafers has a central region and the device further comprising a circular gasket disposed between the central region and the DNA processing sites.

9. The device of claim 8, wherein the DNA processing sites are arranged in a pattern extending radially from the circular gasket toward an outer edge of the wafer.

10. The device of claim 8, further comprising electronics on the wafer and positioned in the central region within the circular gasket.

11. The device of claim 10, further comprising a flex circuit coupled to the electronics on the wafer.

12. The device of claim 1, further comprising a plurality of standoff wafer pitch fiducials formed between the DNA processing sites in concentric circles around radial edges of the DNA processing sites, wherein the plurality of standoff wafer pitch fiducials serve as visual markers for detecting positions of the DNA processing sites on the plurality of wafers.

13. The device of claim 1, further comprising a fluid inlet configured to introduce fluids into the chamber.

14. The device of claim 1, further comprising a fluid exit opening configured to remove fluids from the chamber.

15. The device of claim 1, wherein the DNA processing sites are configured to hold fluid during DNA processing and provide a substrate for DNA synthesis.

16. The device of claim 15, wherein the DNA processing sites further comprise reading mechanisms through which DNA is drawn in response to an applied voltage.

17. The device of claim 1, further comprising a vacuum source configured to create a vacuum within the chamber to add a reagent to the chamber.

18. The device of claim 1, further comprising a circular gasket configured to provide a seal between adjacently mounted wafers.

* * * * *